(12) United States Patent
Moskowitz et al.

(10) Patent No.: US 11,116,642 B2
(45) Date of Patent: Sep. 14, 2021

(54) TOTAL ARTIFICIAL SPINO-LAMINAR PROSTHETIC REPLACEMENT

(71) Applicant: Moskowitz Family LLC, Rockville, MD (US)

(72) Inventors: Nathan C. Moskowitz, Rockville, MD (US); Mosheh T. Moskowitz, Rockville, MD (US); Eric Sugalski, Arlington, MA (US); Ahmnon D. Moskowitz, Rockville, MD (US)

(73) Assignee: Moskowitz Family LLC, Rockville, MD (US)

( * ) Notice: Subject to any disclaimer, the term of this patent is extended or adjusted under 35 U.S.C. 154(b) by 42 days.

(21) Appl. No.: 16/034,545

(22) Filed: Jul. 13, 2018

(65) Prior Publication Data

US 2018/0325690 A1 Nov. 15, 2018

Related U.S. Application Data

(63) Continuation of application No. 15/904,617, filed on Feb. 26, 2018, now Pat. No. 10,022,238, which is a (Continued)

(51) Int. Cl.
*A61F 2/44* (2006.01)
*A61B 17/70* (2006.01)
*A61F 2/30* (2006.01)

(52) U.S. Cl.
CPC ........ *A61F 2/4405* (2013.01); *A61B 17/7071* (2013.01); *A61F 2002/30471* (2013.01); *A61F 2002/30563* (2013.01); *A61F 2002/30578* (2013.01); *A61F 2002/30604* (2013.01); *A61F 2002/30616* (2013.01); *A61F 2002/30624* (2013.01); *A61F 2002/30649* (2013.01); *A61F 2002/30948* (2013.01); *A61F 2002/30952* (2013.01); *A61F 2002/449* (2013.01); *A61F 2310/00023* (2013.01)

(58) Field of Classification Search
CPC .......... A61F 2/44; A61F 2/3094–30942; A61F 2002/30948–3095; A61B 17/7067–7068
See application file for complete search history.

(56) References Cited

U.S. PATENT DOCUMENTS 5,370,692 A * 12/1994 Fink ...................... B29C 64/165
128/898
5,470,333 A 11/1995 Ray
(Continued)

OTHER PUBLICATIONS

ARCH Fixation System. Implants and instruments for open door laminoplasty procedures, Synthes Spine, 2004, 19 pages.
(Continued)

*Primary Examiner* — Eduardo C Robert
*Assistant Examiner* — Michelle C Eckman
(74) *Attorney, Agent, or Firm* — Fish & Richardson P.C.

(57) ABSTRACT

A total artificial spinous process (spino)-laminar prosthesis (TASP-LP) including a body having a portion forming a spinous process extending away from the body, a first lamina portion extending from a first side of the body, and a second lamina portion extending from a second side of the body, wherein the first lamina portion and the second lamina portion are disposed on opposite sides of the spinous process.

20 Claims, 41 Drawing Sheets

Related U.S. Application Data continuation of application No. 12/983,107, filed on Dec. 31, 2010, now Pat. No. 9,901,455, which is a continuation of application No. 12/846,822, filed on Jul. 29, 2010, now abandoned.

(60) Provisional application No. 61/306,926, filed on Feb. 22, 2010, provisional application No. 61/264,648, filed on Nov. 25, 2009.

(56) References Cited

U.S. PATENT DOCUMENTS

| | | | | |
|---|---|---|---|---|
| 5,762,125 | A | 6/1998 | Mastrorio | |
| 6,132,464 | A | 10/2000 | Martin | |
| 6,206,882 | B1 | 3/2001 | Cohen | |
| 6,419,703 | B1* | 7/2002 | Fallin | A61F 2/4405 623/17.11 |
| 6,481,440 | B2 | 11/2002 | Gielen et al. | |
| 6,610,091 | B1* | 8/2003 | Reiley | A61B 17/1671 623/17.11 |
| 6,669,729 | B2 | 12/2003 | Chin | |
| 6,902,580 | B2 | 6/2005 | Fallin et al. | |
| 7,090,698 | B2* | 8/2006 | Goble | A61F 2/4405 623/17.11 |
| 7,282,064 | B2 | 10/2007 | Chin | |
| 7,377,942 | B2 | 5/2008 | Berry | |
| 7,567,834 | B2* | 7/2009 | Clayton | A61B 5/06 600/424 |
| 7,604,652 | B2 | 10/2009 | Arnin et al. | |
| 7,837,711 | B2* | 11/2010 | Bruneau | A61B 17/7067 606/246 |
| 7,846,188 | B2 | 12/2010 | Moskowitz et al. | |
| 7,850,732 | B2 | 12/2010 | Heinz | |
| 7,854,765 | B2 | 12/2010 | Moskowitz et al. | |
| 7,854,766 | B2 | 12/2010 | Moskowitz et al. | |
| 7,862,590 | B2 | 1/2011 | Lim et al. | |
| 7,942,903 | B2 | 5/2011 | Moskowitz et al. | |
| 7,951,180 | B2 | 5/2011 | Moskowitz et al. | |
| 8,066,741 | B2 | 11/2011 | Fallin et al. | |
| 8,118,846 | B2 | 2/2012 | Leither et al. | |
| 8,147,528 | B2 | 4/2012 | Mazzuca et al. | |
| 8,172,875 | B2 | 5/2012 | Taylor | |
| 8,226,688 | B2 | 7/2012 | Alain | |
| 8,251,891 | B2 | 8/2012 | Moskowitz et al. | |
| 8,252,026 | B2 | 8/2012 | Joshi | |
| 8,425,515 | B2* | 4/2013 | Gamache | A61B 17/7071 606/246 |
| 8,435,265 | B2 | 5/2013 | Konieczynski et al. | |
| 8,535,379 | B2 | 9/2013 | Moskowitz et al. | |
| 8,864,798 | B2 | 10/2014 | Weiman et al. | |
| 9,295,497 | B2* | 3/2016 | Schoenefeld | A61B 17/1757 |
| D775,335 | S* | 12/2016 | Frey | D24/140 |
| 9,526,533 | B1* | 12/2016 | Aranibar | A61B 17/7067 |
| 9,717,541 | B2* | 8/2017 | Lee | A61B 17/7059 |
| 10,064,726 | B1* | 9/2018 | Wei | A61F 2/30942 |
| 10,292,770 | B2* | 5/2019 | Ryan | A61B 34/10 |
| 2002/0007294 | A1* | 1/2002 | Bradbury | G16H 10/60 705/2 |
| 2002/0095155 | A1 | 7/2002 | Michelson | |
| 2003/0040797 | A1 | 2/2003 | Fallin et al. | |
| 2003/0050700 | A1 | 3/2003 | Kihara | |
| 2003/0195514 | A1 | 10/2003 | Trieu et al. | |
| 2004/0030388 | A1 | 2/2004 | Null et al. | |
| 2004/0117015 | A1* | 6/2004 | Biscup | G16H 50/50 623/16.11 |
| 2004/0133276 | A1* | 7/2004 | Lang | A61F 2/30756 623/14.12 |
| 2004/0152970 | A1* | 8/2004 | Hunter | A61B 17/025 600/424 |
| 2004/0158245 | A1 | 8/2004 | Chin | |
| 2005/0033434 | A1* | 2/2005 | Berry | A61B 17/7064 623/17.14 |
| 2005/0119657 | A1 | 6/2005 | Goldsmith | |
| 2005/0149021 | A1* | 7/2005 | Tozzi | A61B 17/7058 606/280 |
| 2005/0228377 | A1 | 10/2005 | Chao et al. | |
| 2005/0228381 | A1 | 10/2005 | Kirschman | |
| 2006/0036246 | A1 | 2/2006 | Carl et al. | |
| 2006/0036324 | A1 | 2/2006 | Sachs et al. | |
| 2006/0058790 | A1 | 3/2006 | Carl et al. | |
| 2006/0161154 | A1 | 7/2006 | McAfee | |
| 2006/0241610 | A1 | 10/2006 | Lim et al. | |
| 2006/0241642 | A1* | 10/2006 | Amin | A61F 2/4611 606/90 |
| 2006/0264948 | A1 | 11/2006 | Williams | |
| 2006/0282020 | A1 | 12/2006 | Bertagnoli et al. | |
| 2007/0083266 | A1* | 4/2007 | Lang | A61F 2/30756 623/17.11 |
| 2007/0118243 | A1* | 5/2007 | Schroeder | G16H 50/50 700/118 |
| 2007/0191834 | A1 | 8/2007 | Bruneau et al. | |
| 2007/0191950 | A1 | 8/2007 | Arnin et al. | |
| 2007/0198091 | A1* | 8/2007 | Boyer | A61B 17/7064 623/17.13 |
| 2007/0233068 | A1 | 10/2007 | Bruneau et al. | |
| 2007/0233269 | A1* | 10/2007 | Steines | A61F 2/30756 623/20.21 |
| 2007/0276501 | A1* | 11/2007 | Betz | A61F 2/30942 623/17.16 |
| 2008/0027549 | A1 | 1/2008 | Kirschman | |
| 2008/0195211 | A1* | 8/2008 | Lin | A61F 2/30942 623/17.16 |
| 2008/0281360 | A1* | 11/2008 | Vittur | A61F 2/44 606/248 |
| 2008/0281361 | A1 | 11/2008 | Vittur et al. | |
| 2009/0018585 | A1 | 1/2009 | Reiley | |
| 2009/0222103 | A1* | 9/2009 | Fitz | A61F 2/30942 623/18.11 |
| 2009/0276045 | A1* | 11/2009 | Lang | A61F 2/30756 623/14.12 |
| 2009/0326592 | A1* | 12/2009 | Butler | A61B 17/7058 606/286 |
| 2010/0057127 | A1 | 3/2010 | McGuire et al. | |
| 2010/0174315 | A1* | 7/2010 | Scodary | A61B 17/7052 606/248 |
| 2010/0191100 | A1* | 7/2010 | Anderson | A61B 5/055 600/424 |
| 2010/0217322 | A1* | 8/2010 | Predick | A61B 17/7044 606/250 |
| 2010/0217336 | A1* | 8/2010 | Crawford | G16H 50/50 606/86 R |
| 2010/0249842 | A1* | 9/2010 | Mir | A61B 17/7052 606/250 |
| 2010/0268277 | A1 | 10/2010 | Bruneau et al. | |
| 2011/0125269 | A1* | 5/2011 | Moskowitz | A61B 17/7071 623/17.11 |
| 2011/0125306 | A1* | 5/2011 | Blay | A61F 2/28 700/98 |
| 2011/0144692 | A1 | 6/2011 | Saladin et al. | |
| 2011/0160772 | A1 | 6/2011 | Arcenio et al. | |
| 2011/0172709 | A1 | 7/2011 | Lyons et al. | |
| 2011/0270397 | A1* | 11/2011 | Mac-Thiong | A61B 17/7071 623/17.11 |
| 2011/0295378 | A1* | 12/2011 | Bojarski | A61F 2/30942 623/20.35 |
| 2011/0307012 | A1* | 12/2011 | Mir | A61B 17/7052 606/251 |
| 2011/0319745 | A1* | 12/2011 | Frey | A61B 17/15 600/407 |
| 2012/0010711 | A1* | 1/2012 | Antonyshyn | A61F 2/2875 623/16.11 |
| 2012/0016419 | A1 | 1/2012 | Aflatoon | |
| 2012/0035728 | A1 | 2/2012 | Fallin et al. | |
| 2012/0143253 | A1 | 6/2012 | Reiley | |
| 2012/0158060 | A1* | 6/2012 | Abrahams | A61B 17/7052 606/248 |
| 2012/0209328 | A1 | 8/2012 | Alamin et al. | |
| 2012/0209394 | A1* | 8/2012 | Bojarski | A61F 2/30942 623/20.32 |
| 2012/0215261 | A1 | 8/2012 | Massoudi | |

(56) References Cited

U.S. PATENT DOCUMENTS

| | | |
|---|---|---|
| 2012/0259366 A1 | 10/2012 | Lange |
| 2012/0259367 A1 | 10/2012 | Lange |
| 2012/0296377 A1 | 11/2012 | Ferree et al. |
| 2012/0296379 A1 | 11/2012 | Morancy-Meister et al. |
| 2012/0310364 A1* | 12/2012 | Li ................. A61F 2/2803 623/23.55 |
| 2013/0197641 A1* | 8/2013 | Shepard ............ A61B 17/7071 623/17.11 |
| 2013/0211524 A1* | 8/2013 | Hugues ............ A61B 17/7071 623/17.11 |
| 2013/0218163 A1* | 8/2013 | Frey ................. A61B 5/0488 606/87 |
| 2013/0218282 A1* | 8/2013 | Hunt ................. A61F 2/30 623/19.11 |
| 2014/0025181 A1* | 1/2014 | Vanasse ............ A61F 2/28 623/23.55 |
| 2014/0052183 A1* | 2/2014 | Freese .............. A61B 17/0401 606/248 |
| 2014/0350614 A1* | 11/2014 | Frey ................. A61B 17/1757 606/86 R |
| 2015/0198943 A1* | 7/2015 | Kotlus ............... B22F 3/1055 623/17.16 |
| 2016/0007983 A1* | 1/2016 | Frey ................. A61B 17/56 623/17.16 |
| 2016/0015465 A1* | 1/2016 | Steines .............. A61B 34/10 623/18.11 |
| 2016/0030067 A1* | 2/2016 | Frey ................. A61B 17/1757 606/86 A |
| 2016/0045317 A1* | 2/2016 | Lang ................. A61F 2/30942 700/98 |
| 2016/0324664 A1* | 11/2016 | Piron ................. A61F 2/46 |
| 2017/0056179 A1* | 3/2017 | Lorio ................. B22F 3/1055 |
| 2017/0135706 A1* | 5/2017 | Frey ................. A61B 17/1703 |
| 2017/0143494 A1* | 5/2017 | Mahfouz ............ A61B 34/20 |
| 2017/0143502 A1* | 5/2017 | Yadin ................ B33Y 80/00 |
| 2017/0165081 A1 | 6/2017 | Fallin |
| 2017/0249440 A1* | 8/2017 | Lang ................. B22F 3/1055 |
| 2017/0252176 A1* | 9/2017 | Tacca ................ A61B 17/7071 |
| 2017/0290651 A1* | 10/2017 | Konig ................ A61F 2/0077 |
| 2017/0325852 A1 | 11/2017 | Chen |
| 2017/0354502 A1* | 12/2017 | Ryu .................. A61F 2/28 |
| 2018/0005548 A1* | 1/2018 | Blair-Pattison ....... A61L 27/20 |
| 2018/0008349 A1* | 1/2018 | Gillman ............. A61B 17/7062 |
| 2018/0055643 A1* | 3/2018 | Castro ............... B33Y 10/00 |
| 2018/0147062 A1* | 5/2018 | Ay ................... A61F 2/30942 |
| 2018/0271602 A1* | 9/2018 | Frey ................. A61B 34/10 |
| 2018/0303616 A1* | 10/2018 | Bhattacharyya ..... A61F 2/30942 |
| 2019/0239868 A1* | 8/2019 | Attenborough .. A61B 17/00491 |
| 2019/0254826 A1* | 8/2019 | Lang ................. A61F 2/30756 |

OTHER PUBLICATIONS

Heller and Wang, "Centerpiece Plate Fixation System: Surgical Technique," Medtronic Sofamor Danek, 2005, 27 pages.

* cited by examiner

400

400

600

700

800

900

900

TOTAL ARTIFICIAL SPINO-LAMINAR PROSTHETIC REPLACEMENT

CROSS-REFERENCE TO RELATED APPLICATIONS

This application is a Continuation Application of U.S. application Ser. No. 15/904,617, filed on Feb. 26, 2018, now U.S. Pat. No. 10,022,238, which is a Continuation Application of U.S. application Ser. No. 12/983,107, filed on Dec. 31, 2010, now U.S. Pat. No. 9,901,455, which is a Continuation Application of U.S. application Ser. No. 12/846,822, filed on Jul. 29, 2010, for which priority is claimed under 35 U.S.C. § 120, and also claims the benefit of priority under 35 U.S.C. § 119(e) of U.S. Provisional Patent Application No. 61/264,648, filed Nov. 25, 2009, and entitled "TOTAL ARTIFICIAL SPINO-LAMINAR PROSTHETIC REPLACEMENT", and U.S. Provisional Patent Application No. 61/306,926, filed Feb. 22, 2010, and entitled "TOTAL ARTIFICIAL SPINO-LAMINAR PROSTHETIC REPLACEMENT", the entire contents of all of the above identified patent applications are hereby incorporated by reference in their entirety.

FIELD OF THE INVENTION

The present invention is directed to a unique total artificial spinous process (spino)-laminar prosthesis (hereinafter "TASP-LP"), and a method of implanting a TASP-LP, and more particularly, to customized patient specific TASP-LP devices including single modular replacement TASP-LP devices of varying lengths and widths, and double and triple modular replacement TASP-LP devices, along with methods of performing single-level surgical laminectomy and multi-level laminectomies using such devices.

BACKGROUND OF THE INVENTION

Posterior spinal laminectomies are performed to decompress the spinal cord and/or nerve roots contained within the spinal canal. Decompressive laminectomies are performed to relieve degenerative stenosis, herniated/bulging discs, and traumatic stenosis. In addition, they are performed in order to access the spinal canal to enable the removal and/or treatment of benign or malignant tumors, vascular lesions, abscesses, other masses, syrinxes, and a host of other conditions.

Posterior laminectomies can be performed on every spinal element throughout the entire spine including cervical, thoracic and lumbar. Laminectomies leave the posterior neural elements exposed without their native protection provided by dorsal protective lamina/spinous processes, and can lead to short and/or long term deformity and/or kyphosis. Delayed kyphosis, particularly in the cervical spine is typically remedied with the performance of posterior instrumented fusions which have an increased risk of neurovascular complications.

Kyphotic deformities secondary to laminectomies are more prevalent in the cervical spine. As a result of this multiple versions of a technique called laminoplasty have been developed for the cervical spine. This technique entails, opening up the lamina on one side, and using a variety of plates and screws to reattach the opened lamina to the remaining native lamina. These techniques can be cumbersome, time consuming, and also may have increased likelihood of dural tears, and nerve root injuries compared to the performance of straight forward laminectomies. However, laminoplasties as a result of protecting the cervical dura may have a less likely chance of leading to delayed kyphotic deformities.

Currently there is limited attention/technology developed for laminoplasty techniques related to thoracic/or lumbar spines. There are no other known devices that provide total artificial spinous process-laminar replacements (prostheses) mechanically designed for the explicit purposes of laminoplasty, i.e. to enlarge the diameter of the spinal canal and reconstruct the natural spinolaminar anatomy to protect exposed neural elements.

U.S. Application to Vittur et.al (Spinous process implants and methods; U.S. Pub No: US 2008/0281360 A1) describes embodiments of a replacement spinous process with a flat or concave single piece laminar portion extending anteriorly and inferiorly, and not laterally. It's lack of concavity when applied to the spine does not allow for the expansion of the dural spinal space, which is mandatory for a stenotic thecal sac decompression, and hence is not suitable for the purposes of a decompressive laminoplasty/laminectomy. Its primary purpose is to replace injured spinous processes, in order to "provide and maintain separation between spinous processes". The device is predominantly contoured to fit an inter-spinous spacer (specifically the DIAM spinal stabilization system of Medtronic), to distract spinous processes. It is not attached directly to the lamina. It is somewhat cumbersome with laterally protruding separate or built-in connecting elements which in turn are attached to anchors which in turn are secured to pedicle screws. No embodiment is capable of replacing more than one spinal element.

Other device embodiments presented by Vittur et.al. (Posterior stabilization and spinous process systems and methods; U.S. Pub. No. US 2008/0281361 A1, Pub date Nov. 13, 2008) include multiple embodiments of spinous process replacements which do not in any way geometrically reproduce the spinous process anatomy, and are essentially devices designed to crosslink two elongated parallel bars, which in turn are attached to pedicle screws. This device "is integrated with posterior stabilization instrumentation so that interspinous stabilization procedures can be completed even if the spinous process of the patient is removed . . . " This device is not designed, or considered, to be, a total spinolaminar replacement, nor is it suitable for a laminectomy/laminoplasty. It does not attach directly to the spine, rather it is attached to parallel bars, which in turn are secured by pedicle screws which are attached to the spine.

U.S. Applications and Patent to Bruneau et. al (Artificial Spinous Process for the Sacrum and Methods of its use; U.S. 2007/0191834 A1; Pub Aug. 16, 2007), U.S. Pat. No. 7,837,711 B2; Patented Nov. 23, 2010, and U.S. 2010/0268277 A1; Pub Oct. 21, 2010) describe a device that attaches to the sacrum and provides a support for positioning an implant to dampen the relative movements during flexion and extension exclusively between the sacrum and the fifth lumbar vertebrae. The purpose of this implant is to fortify, not replace, the S1 (first sacral) vertebrae, which may not be well defined and therefore inadequate to support an implant. Specifically, the device is not a spinolaminar replacement or a spinous process replacement. It is positioned along the lateral sides of the S1 process, and its lateral extensions are uniquely designed only for the sacral anatomy. Another embodiment described by Bruneau et.al has extensions which then connect to anchors which are screwed into the sacrum. This device is not adaptable for any position of the spine other than L5-S1. Furthermore, is it not directly attached to the lamina, but rather has lateral protruding elements which in turn are attached to lateral extensions which in turn are attached to sacral screws. This device replaces neither lamina nor spinous processes.

U.S. Patent to Gielen et al. (Lamina Prosthesis for delivery of medical treatment; U.S. Pat. No. 6,481,440 B2; Nov. 19, 2002) disclose a unilateral laminar prosthetic which only replaces a portion of a lamina unilaterally and is configured with means for delivering a variety of medical treatments, such as electrodes, fluid channels, catheters and drugs. It is not secured to remaining lamina; rather it is secured to vertebral bodies with conventional bonding glue or similar technology. This device substitutes a portion of a hemilamina for the explicit purposes of delivering ancillary treatment. It is not considered a total spinolaminar replacement, nor does its design reflect such a purpose.

U.S. Application to Williams (Bone anchored surgical mesh; Pub. No. US 2006/0264948 A1; Published Nov. 23, 2006) describes a bone anchored surgical mesh to cover the spinal cord after a laminectomy. This perforated mesh offers an inadequate protective cover of posterior spinal elements, and lacks the strength of a total spinolaminar replacement which recreates the solid anatomy of the spinal posterior elements which is necessary to protect and strengthen the post-laminectomy spine.

U.S. Application to Mir (Spinous Process cross-link; US 2010/0249842 A1; Pub: Sep. 30, 2010) presents a prosthetic spinous process crosslink similar to Vittur et al. which attaches to the spine by gripping feet extensions which grip rods which are secured to pedicle screws, or directly grip pedicle screws.

SUMMARY OF THE INVENTION

These problems and others are addressed by the present invention, an exemplary embodiment of which includes a total artificial spinous process (spino)-laminar prosthesis (TASP-LP) which is specifically designed as a laminoplasty alternative, i.e. to expand the spinal canal by the performance of a laminectomy and to replace one or multiple total spinolaminar units in order to reconstitute the strength and structural integrity of the natural pre-laminectomy spinolaminar anatomy, as well as to protect the underlying posterior spinal neural elements.

Hence, the present invention provides an exemplary single unit TASP embodiment that reproduces the natural concavity of the lamina, extends laterally (right and left), and not anteriorly/posteriorly, in order to specifically accommodate and allow the expansion of the decompressed stenotic spine. Furthermore, these lamina fan out with lateral extensions that are parallel to the remaining lamina (outside the laminectomy field), with perforations for translaminar or facet screws which allows for the simple direct attachment of the prosthesis to the spine. The present invention provides important advantages in that there is no need for an additional set of cumbersome connecting elements which connect to separate anchors, parallel bars, rods, and/or pedicle screws, all of which add complexity, time, and morbidity to the surgical procedure. Furthermore, the exemplary single unit embodiments can replace one, two or three spinolaminar units at a time, unlike any of the conventional devices mentioned above. In addition, the exemplary embodiments can include either laminar hinged extensions or artificial spinous process hinges to actively widen the TASP to account for intra and inter-patient spinal canal width variability, and to accommodate for inter and inter-patient laminar topography variability. These exemplary embodiments allow custom fitting of the device for all different inter and intra-patient anatomies. Furthermore, exemplary cervical and thoracic/lumbar TASPs are designed completely differently from each other in order to account for differences between cervical and thoracic/lumbar anatomies, e.g. the spinous process of an exemplary cervical TASP is bifid replicating the natural cervical anatomy, among other significant differences detailed below.

For example, the above-identified problems and others are addressed by the present invention, an exemplary embodiment of which includes a total artificial spinous process (spino)-laminar prosthesis (TASP-LP) comprising a body having a portion forming a spinous process extending away from the body; a first lamina portion extending from a first side of the body; and a second lamina portion extending from a second side of the body, wherein the first lamina portion and the second lamina portion are disposed on opposite sides of the spinous process.

The spinous process can include an opening for muscle or fascia suture attachment, or a plurality of openings for muscle or fascia suture attachment. The spinous process can include, for example, two lobes mimicking a natural anatomy of a spinal element, or a single lobe mimicking a natural anatomy of a spinal element. Each of the two lobes can include an opening for muscle or fascia suture attachment.

In another embodiment, each of the first lamina portion and the second lamina portion can include an opening for receiving an attachment device for securing the first lamina portion and the second lamina portion to natural lamina of a spinal element.

The TASP-LP can include an attachment device engaging the opening. The attachment device can include, but is not limited to, for example, a translaminar screw, a flathead screw, a self-tapping screw, etc. Other suitable attachment devices are contemplated by the invention. For example, the attachment device can include a pin, such as a flat pin, a round pin, a pin having hooks, and a pin having ridges, or another attachment device, such as a staple. The staple can include a flat portion, a round portion, a portion having hooks, or a portion having ridges.

A surface of each of the first lamina portion and the second lamina portion can include a recess surrounding the opening for receiving a head of the attachment device such that the head of the attachment device is countersunk into or flush with the surface. A surface of each of the first lamina portion and the second lamina portion can engage the attachment device to lock the attachment device with the surface. In other embodiments, each of the first lamina portion and the second lamina portion can include a plurality of openings for receiving attachment devices. In another embodiment, the TASP-LP can include a plurality of attachment devices respectively engaging the plurality of openings.

In another exemplary embodiment, each of the first lamina portion and the second lamina portion can include an underside facing away from the body and having a contoured portion. A contour of the contoured portion of the underside of the first lamina portion can be different than a contour of the contoured portion of the underside of the second lamina portion.

In another exemplary embodiment, each of the first lamina portion and the second lamina portion can includes a relief opening or groove that permits each of the first lamina portion and the second lamina portion to flex. In other embodiments, each of the first lamina portion and the second lamina portion can includes a pair of openings for receiving attachment devices, and each of the first lamina portion and the second lamina portion can include a relief opening or groove between the pair of openings that permits each of the first lamina portion and the second lamina portion to flex along an area adjacent to each of the pair of openings.

In another exemplary embodiment, each of the first lamina portion and the second lamina portion can includes a thinned portion having a thickness that is less than a thickness of an adjacent portion, thereby permitting each of the first lamina portion and the second lamina portion to flex at the thinned portion.

In another exemplary embodiment, the TASP-LP can include a first hinged extension that is movable with respect to the first lamina portion and a second hinged extension that is movable with respect to the second lamina portion. The TASP-LP can include a first hinge pin rotatably coupling the first hinged extension to the first lamina portion; and a second hinge pin rotatably coupling the second hinged extension to the second lamina portion, wherein each of the first hinged extension and the second hinged extension is pivotable with respect to the first lamina portion and the second lamina portion, respectively, for allowing individualized alignment of the first hinged extension and the second hinged extension with natural laminar having differing inclines. Each of the first hinged extension and the second hinged extension can be pivotable between a neutral position that is parallel to a plane of the first lamina portion and the second lamina portion, respectively, an elevated position that is at a positive angle with respect to the plane, and a depressed position that is at a negative angle with respect to the plane.

In another exemplary embodiment, the spinous process can include a first spinous process portion and a second spinous process portion, wherein the first spinous process portion and the second spinous process portion are pivotable with respect to each other to change a distance between the first lamina portion and the second lamina portion, thereby allowing for accommodating for different laminectomy widths. The TASP-LP can include a spinous process hinge rotatably coupling the first spinous process portion and the second spinous process portion. The TASP-LP can include a first hinged extension that is movable with respect to the first lamina portion and a second hinged extension that is movable with respect to the second lamina portion, wherein the spinous process comprises a first spinous process portion and a second spinous process portion, and wherein the first spinous process portion and the second spinous process portion are pivotable with respect to each other to change a distance between the first lamina portion and the second lamina portion.

In another exemplary embodiment, the TASP-LP can include a first hinged extension that is movable with respect to the first lamina portion; a first hinge pin rotatably coupling the first hinged extension to the first lamina portion; a second hinged extension that is movable with respect to the second lamina portion; a second hinge pin rotatably coupling the second hinged extension to the second lamina portion, wherein each of the first hinged extension and the second hinged extension is pivotable with respect to the first lamina portion and the second lamina portion, respectively, for allowing individualized alignment of the first hinged extension and the second hinged extension with natural laminar having differing inclines, and wherein the spinous process comprises a first spinous process portion; a second spinous process portion, and a spinous process hinge rotatably coupling the first spinous process portion and the second spinous process portion, wherein the first spinous process portion and the second spinous process portion are pivotable about the spinous process hinge to change a distance between the first lamina portion and the second lamina portion for allowing for accommodating of different laminectomy widths.

In another exemplary embodiment, one of the body, the spinous process, the first lamina portion, and the second lamina portion comprises titanium. In yet another exemplary embodiment, one of the body, the spinous process, the first lamina portion, and the second lamina portion comprises a bio-compatible material.

In another exemplary embodiment, the TASP-LP can include a second body having a second portion forming a second spinous process extending away from the second body; a third lamina portion extending from a first side of the second body; a fourth lamina portion extending from a second side of the second body, wherein the third lamina portion and the fourth lamina portion are disposed on opposite sides of the second spinous process; a first bridge coupling the first lamina portion of the body to the third lamina portion of the second body; and a second bridge coupling the second lamina portion of the body to the fourth lamina portion of the second body. In an exemplary embodiment, the first lamina portion of the body can be integrally formed with the third lamina portion of the second body; and the second lamina portion of the body can be integrally formed with the fourth lamina portion of the second body.

In another exemplary embodiment, the TASP-LP can include a third body having a third portion forming a third spinous process extending away from the third body; a fifth lamina portion extending from a first side of the third body; a sixth lamina portion extending from a second side of the third body, wherein the fifth lamina portion and the sixth lamina portion are disposed on opposite sides of the third spinous process; a third bridge coupling the third lamina portion of the second body to the fifth lamina portion of the third body; and a fourth bridge coupling the fourth lamina portion of the second body to the sixth lamina portion of the third body.

In another exemplary embodiment, the TASP-LP can include a second body having a second portion forming a second spinous process extending away from the second body; a third lamina portion extending from a first side of the second body; a fourth lamina portion extending from a second side of the second body, wherein the third lamina portion and the fourth lamina portion are disposed on opposite sides of the second spinous process; and a connecting bridge coupling the spinous process of the body to the second spinous process of the second body.

In another exemplary embodiment, the TASP-LP can include a second body having a second portion forming a second spinous process extending away from the second body; a third lamina portion extending from a first side of the second body; a fourth lamina portion extending from a second side of the second body, wherein the third lamina portion and the fourth lamina portion are disposed on opposite sides of the second spinous process; and a connecting bridge coupling the spinous process of the body to the second spinous process of the second body. The spinous process of the body can be integrally formed with the second spinous process of the second body.

In another exemplary embodiment, one of the body, the spinous process, the first lamina portion, and the second lamina portion can include a cavity or area for receiving bone material. Also, one of the body, the spinous process, the first lamina portion, and the second lamina portion can include an opening for muscle or fascia suture attachment.

In another exemplary embodiment of the invention, a total artificial spinous process (spino)-laminar prosthesis (TASP-LP) can include at least two of a first module, a second module, and a third module, wherein each of the first module, the second module, and the third module can comprise a body having a portion forming a spinous process extending away from the body; a first lamina portion extending from a first side of the body; and a second lamina portion extending from a second side of the body, wherein the first lamina portion and the second lamina portion are disposed on opposite sides of the spinous process. The first module can be integrally formed with the second module.

In another exemplary embodiment, the TASP-LP can include the first module, the second module, and the third module, wherein the first module, the second module, and the third module are integrally formed with each other.

In other embodiments, an overall shape, a height, a width, an orientation, and an angulation of the body, the spinous process, the first lamina portion, and the second lamina portion mimics an overall shape, a height, a width, an orientation, and an angulation of a natural spine portion based on a 3-dimensional computer rendition of the natural spine portion.

Another exemplary embodiment of the invention includes a method of implanting the exemplary embodiments of the total artificial spinous process (spino)-laminar prosthesis (TASP-LP) in which the method includes measuring dimensions and geometry of a natural spine portion of a patient; generating a 3-dimensional computer rendition of the natural spine portion; forming the body, the spinous process, the first lamina portion, and the second lamina portion to mimic the natural spine portion based on the 3-dimensional computer rendition of the natural spine portion. In an embodiment of the method, the dimensions and the geometry of the natural spine portion can be generated using MM-CT imaging techniques. An overall shape, a height, a width, an orientation, and an angulation of the body, the spinous process, the first lamina portion, and the second lamina portion can be measured. An overall shape, a height, a width, an orientation, and an angulation of the body, the spinous process, the first lamina portion, and the second lamina portion of the total artificial spinous process (spino)-laminar prosthesis (TASP-LP) are formed to mimic the overall shape, the height, the width, the orientation, and the angulation of the natural spine portion based on the 3-dimensional computer rendition of the natural spine portion.

In another exemplary embodiment, the method can include coupling the total artificial spinous process (spino)-laminar prosthesis (TASP-LP) to a natural spine in place of the natural spine portion.

In another exemplary embodiment, the TASP-LP can include a first hinged extension that is movable with respect to the first lamina portion and a second hinged extension that is movable with respect to the second lamina portion, and the method can include pivoting each of the first hinged extension and the second hinged extension with respect to the first lamina portion and the second lamina portion, respectively, to individually align the first hinged extension and the second hinged extension with individual inclines of the natural spine.

In another embodiment, the spinous process can include a first spinous process portion and a second spinous process portion, wherein the first spinous process portion and the second spinous process portion are pivotable with respect to each other to change a distance between the first lamina portion and the second lamina portion, wherein the method can includes pivoting the first spinous process portion and the second spinous process portion with respect to each other to change the distance between the first lamina portion and the second lamina portion. The TASP-LP can include a first hinged extension that is movable with respect to the first lamina portion and a second hinged extension that is movable with respect to the second lamina portion, wherein the spinous process comprises a first spinous process portion and a second spinous process portion, wherein the first spinous process portion and the second spinous process portion are pivotable with respect to each other to change a distance between the first lamina portion and the second lamina portion, and wherein the method can includes pivoting the first spinous process portion and the second spinous process portion with respect to each other to change the distance between the first lamina portion and the second lamina portion; and pivoting each of the first hinged extension and the second hinged extension with respect to the first lamina portion and the second lamina portion, respectively, to individually align the first hinged extension and the second hinged extension with individual inclines of the natural spine.

Another embodiment is directed to a method of implanting a total artificial spinous process (spino)-laminar prosthesis (TASP-LP), the method comprising measuring dimensions and geometry of a natural spine portion of a patient; generating a 3-dimensional computer rendition of the natural spine portion; forming the at least two of the first module, the second module, and the third module to mimic the natural spine portion based on the 3-dimensional computer rendition of the natural spine portion. The method can include coupling the at least two of the first module, the second module, and the third module to a natural spine in place of the natural spine portion. In the exemplary method, the first module can be integrally formed with the second module. The total artificial spinous process (spino)-laminar prosthesis (TASP-LP) can include the first module, the second module, and the third module, wherein the first module is integrally formed with the second module, and wherein the third module is separate from the first module and the second module. The first module can be integrally formed with the second module and the third module.

An exemplary embodiment of the method can include selecting a combination and arrangement of the first module, the second module, and the third module based on a width and a length of the natural spine portion; and coupling the selected combination and arrangement of the first module, the second module, and the third module to a natural spine in place of the natural spine portion.

An embodiment of the present invention is directed to a unique total artificial spinous process (spino)-laminar prosthesis (hereinafter "TASP-LP") that is implanted dorsally onto the spine after the performance of a spinal laminectomy. A single-level surgical laminectomy entails the removal of a single unit comprising two lamina, right and left, and a single mid-line spinous process. Multilevel laminectomies entail the removal of two or more of these units. The exemplary embodiments of a total artificial spinous process-laminar replacement can be tailor-made to address the multiplicity of laminar-spinous process units removed as a result of a laminectomy in need of artificial replacement/reconstruction. The TASP-LP therefore can include, for example, single modular replacement embodiments of varying lengths and widths addressing single and multiple spino-laminar (SL) unit replacements. In addition, other exemplary embodiments can include double and triple modular embodiments which along with single modules can create hybrid prosthetics for multi-level SL unit replacements.

Other exemplary TASP-LP embodiments can include, for example: a) a device with expandable hinged spinolaminar wings that can accommodate different laminectomy widths, b) a device with hinged laminar extensions which can accommodate individualized laminar inclines, and c) a device with both hinged expandable spinous process-laminar wings and hinged laminar extensions.

An exemplary embodiment of the invention can further individualize the device by using MRI-CT imaging techniques to accurately measure precise spinous process-laminar dimensions and geometry of a particular patient in order to enable highly accurate tailor-made manufactured computerized modular reconstructions for different individuals.

The exemplary embodiments of the invention can obviate the need for cumbersome and complicated laminoplasties, and also serve to recreate normal spinal anatomy after the performance of deforming and potentially destabilizing laminectomies.

The exemplary embodiments of the present invention address the anatomical deficiencies created by the performance of a spinal laminectomy, and seek to artificially recreate the normal spino-laminar anatomy after a laminectomy.

The exemplary embodiments of the invention can provide important advantages, for example, including:

1) protecting the dura of spinal cord and/or nerve roots from traumatic exposure;

2) providing an artificial muscle/facial point of attachment, therefore replicating the normal function of the spinous processes; and/or 3) preventing kyphotic deformity and instability of the spine thereby obviating the need for simultaneous or delayed posterior fusions which increase the risk of nerve root, spinal cord or vascular injuries.

Furthermore, the exemplary embodiments of the invention may provide important advantages over conventional devices and methods associated with laminoplasties in the cervical spine in that the exemplary embodiments may be less cumbersome, takes less time to install, and have lower risk of cord, nerve root injury or dural tear/spinal fluid leak. Moreover, the application of the exemplary embodiments of the invention to post thoracic and lumbar spinal laminectomies, may decrease the risk of spinal deformity, increase protection of spinal elements, decrease the need for fusions, and hence decrease the overall risk of spinal laminectomies, thereby improving overall quality of life for the recipient of the TASP-LP.

In another embodiment, a set or kit of a plurality of prostheses can be provided, each having different standard sizes, such that a surgeon easily can select one or more appropriately sized prostheses. The selected prosthesis each can have the same size or different sizes depending on the dimensions of the natural spinal portions of a given recipient.

Other features and advantages of the present invention will become apparent to those skilled in the art upon review of the following detailed description and drawings.

BRIEF DESCRIPTION OF THE DRAWINGS

These and other aspects and features of embodiments of the present invention will be better understood after a reading of the following detailed description, together with the attached drawings, wherein.

and single according to an exemplary embodiment (Embodiment IA) TASP-LP modules inserted into the Thoracic/Lumbar spine.

Figure 6A:
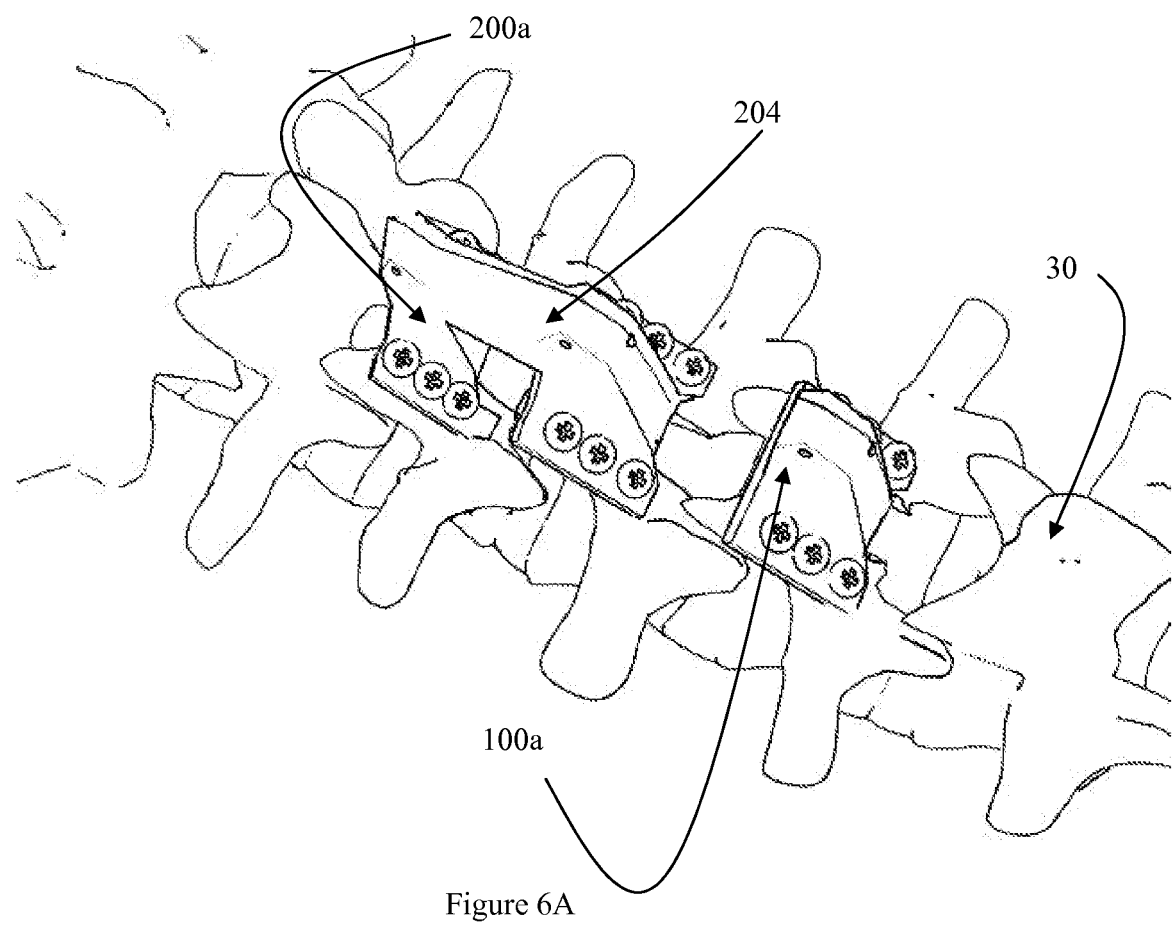
FIG. 6A illustrates a superior-oblique view of a double according to an exemplary embodiment (Embodiment IB) inserted into the Lumbar spine and a hybrid of double according to an exemplary embodiment (Embodiment IB)
Figure 6B:
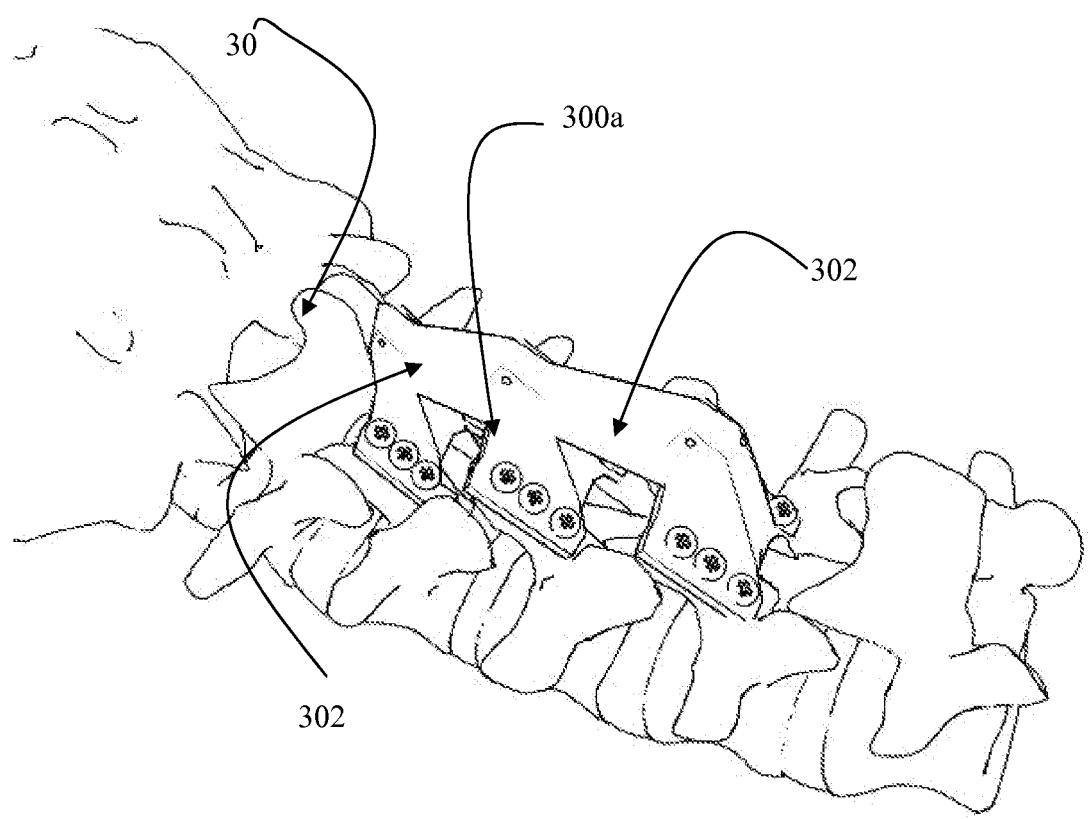

FIG. 6B illustrates a superior-oblique view of a triple according to an exemplary embodiment (Embodiment IC) of Thoracic-Lumbar TASP-LP modules inserted into the Lumbar spine.

Figure 7A:
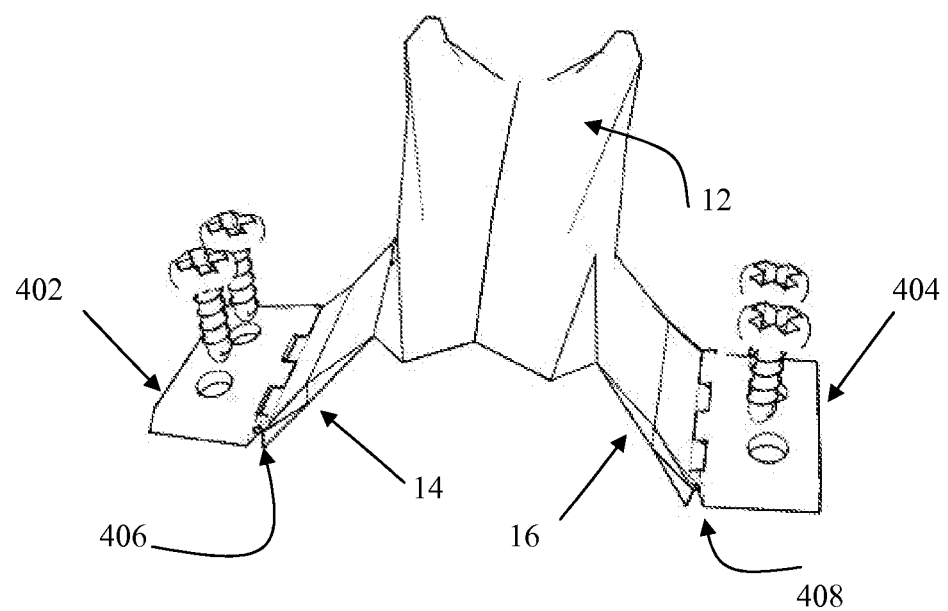

FIG. 7A illustrates a cervical TASP-LP with laminar hinged extensions in a neutral position according to an exemplary embodiment (Embodiment II).

Figure 7B:
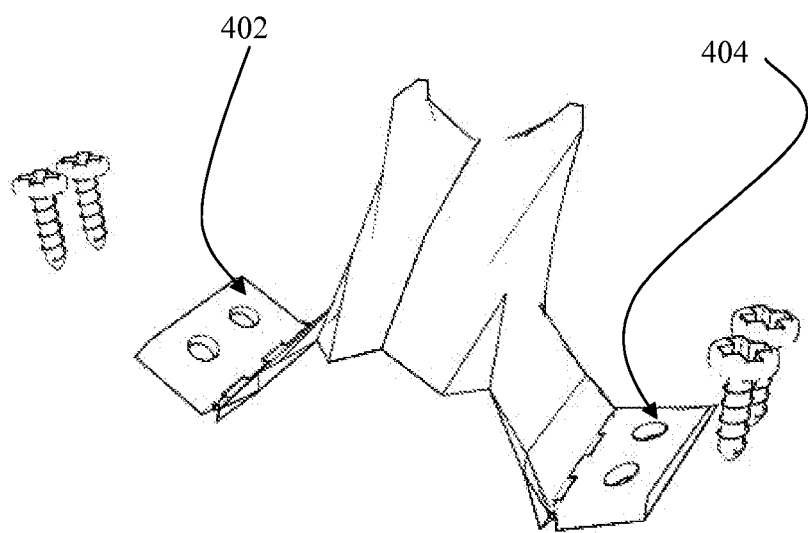

FIG. 7B illustrates a cervical TASP-LP with laminar hinged extensions in an elevated position according to an exemplary embodiment (Embodiment II).

Figure 7C:
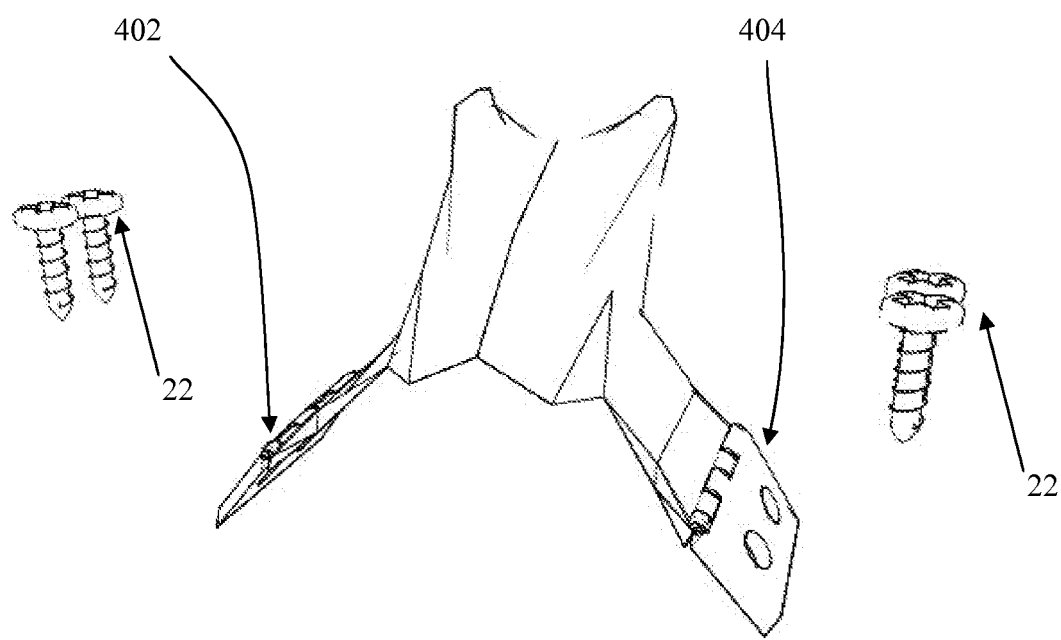

FIG. 7C illustrates a cervical TASP-LP with laminar hinged extensions in a depressed position according to an exemplary embodiment (Embodiment II).

Figure 7D:
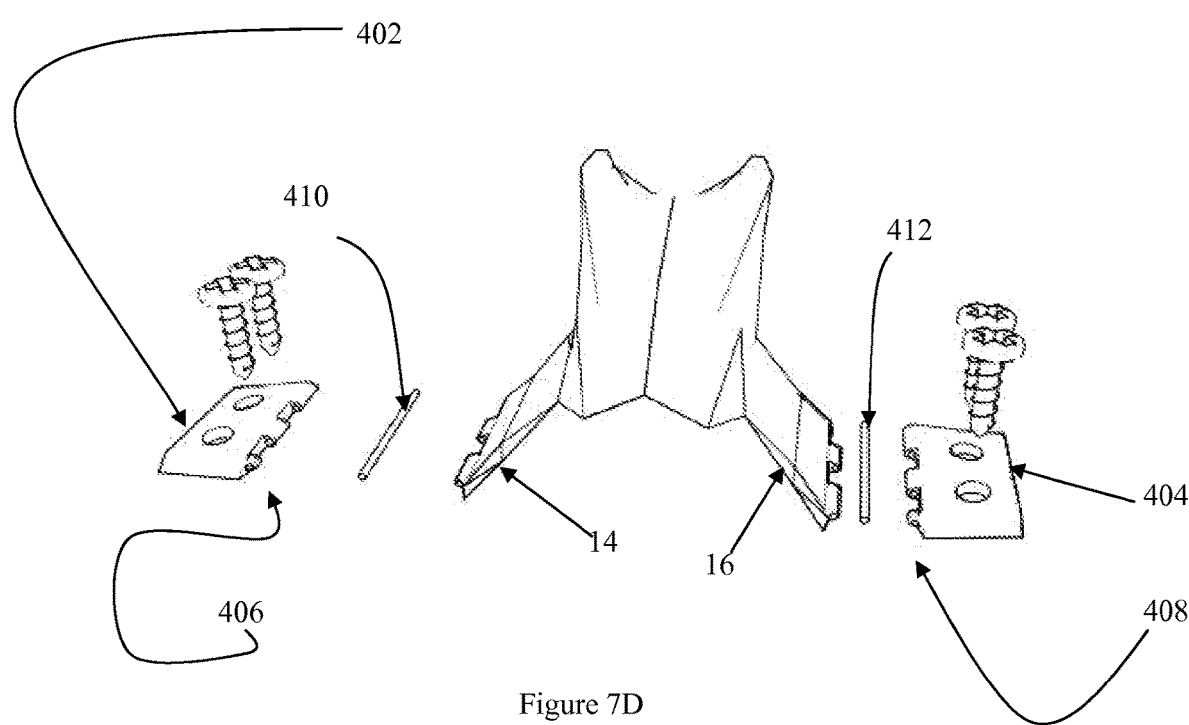

FIG. 7D illustrates an exploded view of the cervical TASP-LP according to an exemplary embodiment (Embodiment II).

Figure 8A:
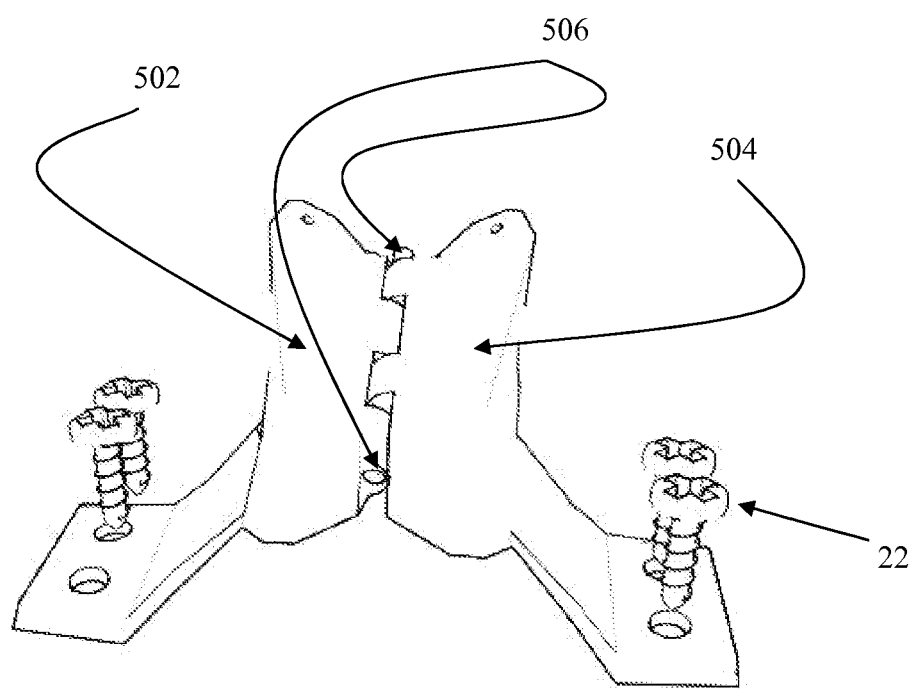

FIG. 8A illustrates a cervical TASP-LP with spino-laminar hinged extensions in a neutral position according to an exemplary embodiment (Embodiment III).

Figure 8B:
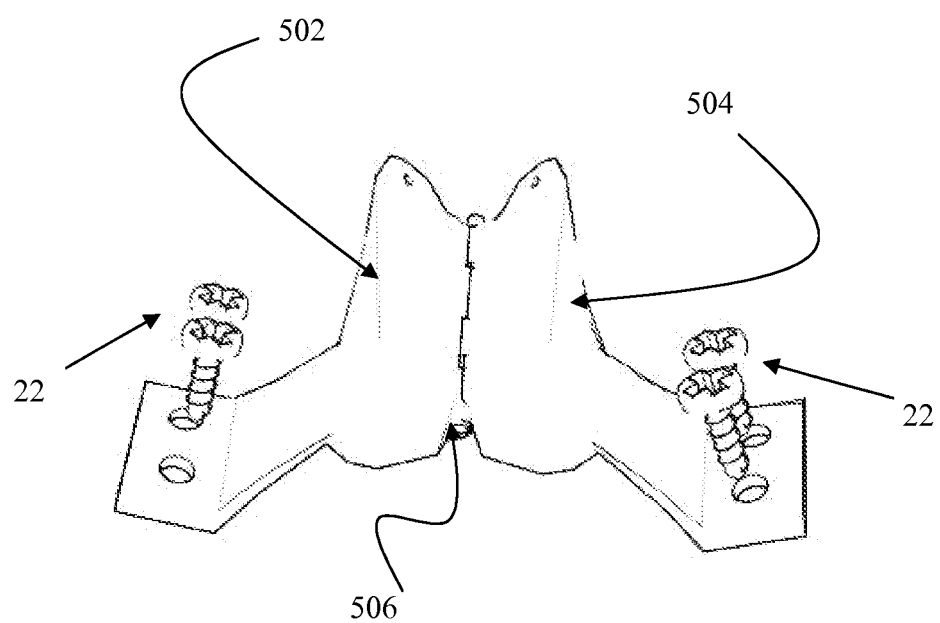

FIG. 8B illustrates a cervical TASP-LP with spino-laminar hinged extensions in an elevated position according to an exemplary embodiment (Embodiment III).

Figure 8C:
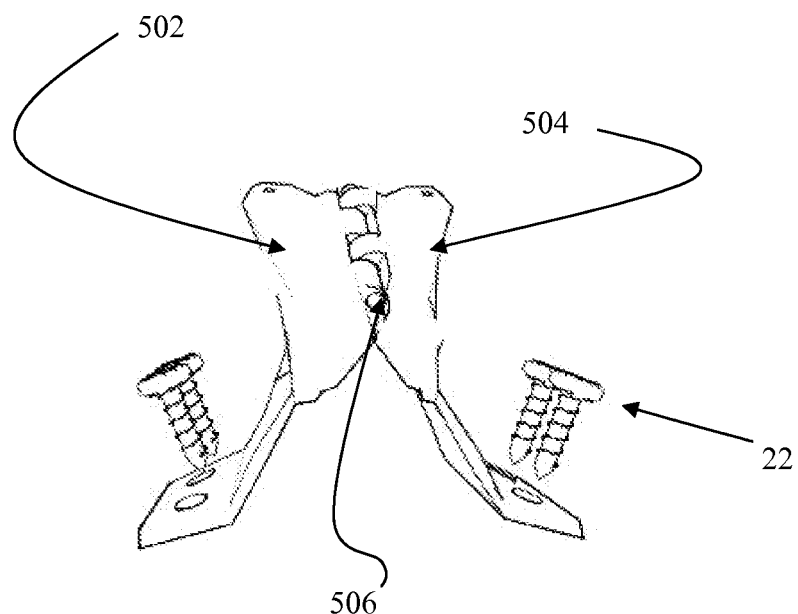

FIG. 8C illustrates a cervical TASP-LP with spino-laminar hinged extensions in a depressed position according to an exemplary embodiment (Embodiment III).

Figure 8D:
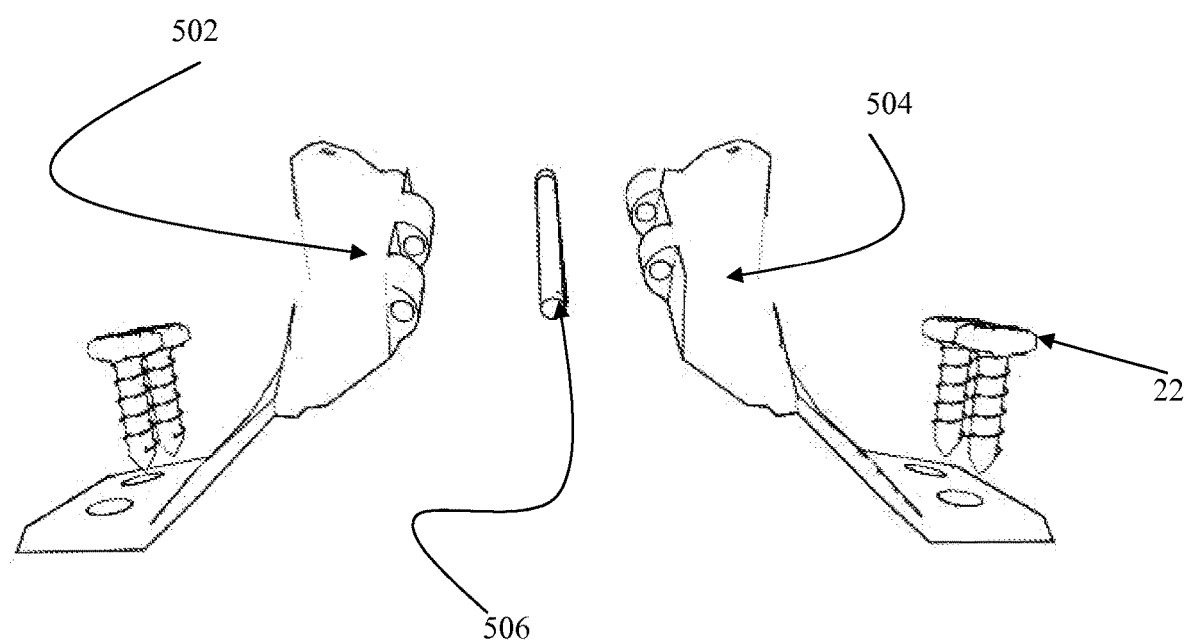

FIG. 8D illustrates an exploded view of the cervical TASP-LP according to an exemplary embodiment (Embodiment III).

Figure 9A:
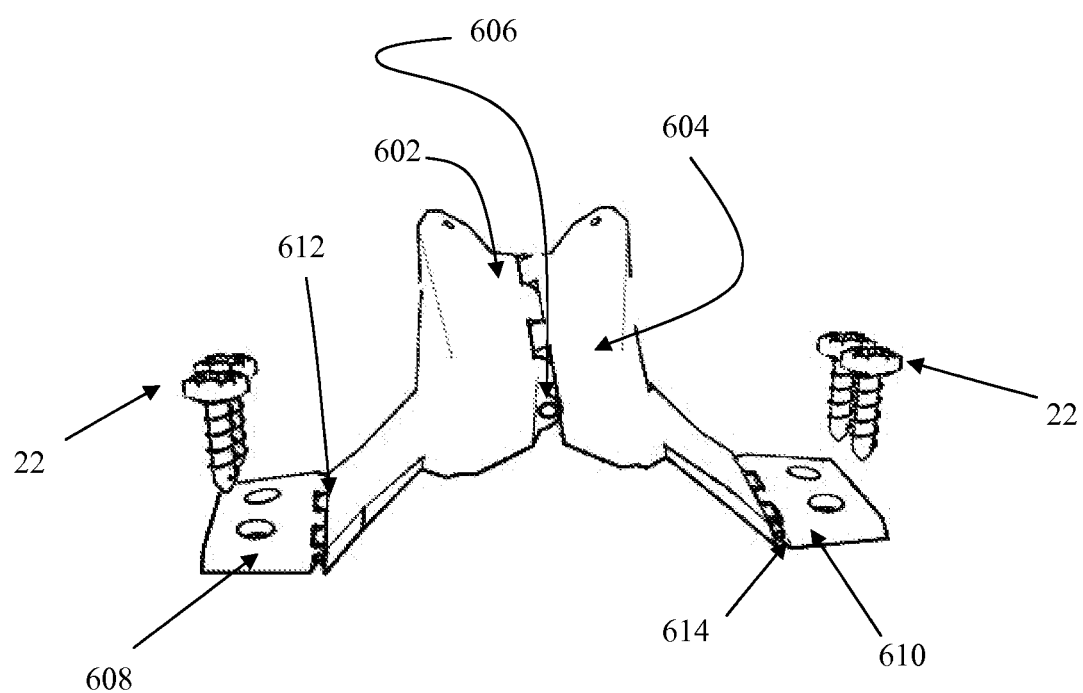

FIG. 9A illustrates an anterior-posterior view of the cervical TASP-LP according to an exemplary embodiment (Embodiment IV).

Figure 9B:
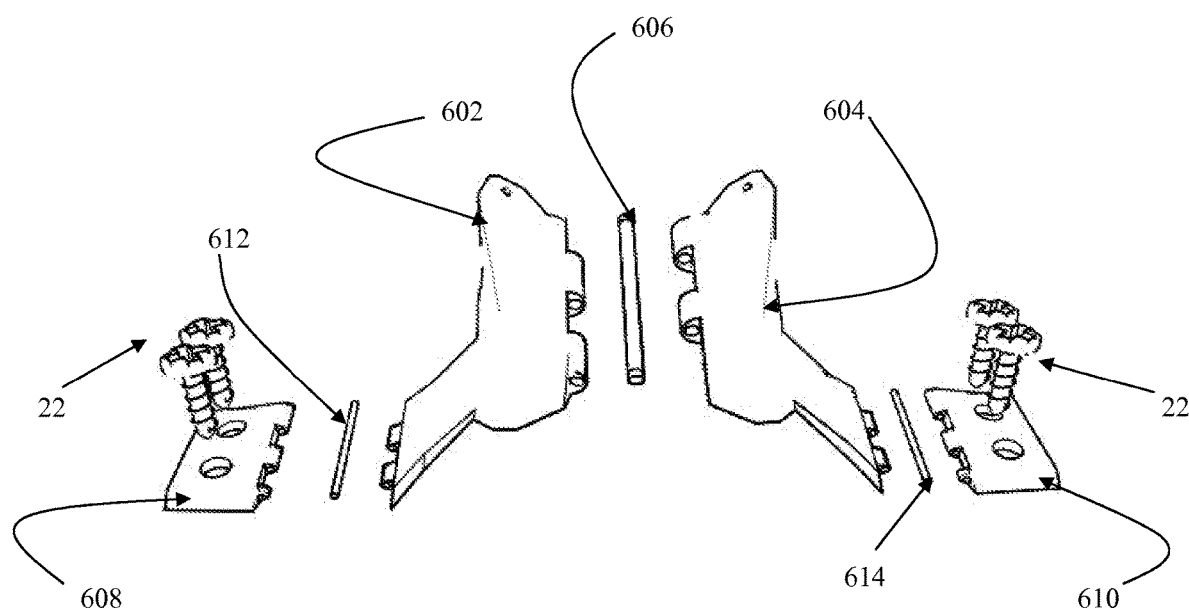

FIG. 9B illustrates an exploded view of the cervical TASP-LP according to an exemplary embodiment (Embodiment IV).

Figure 10A:
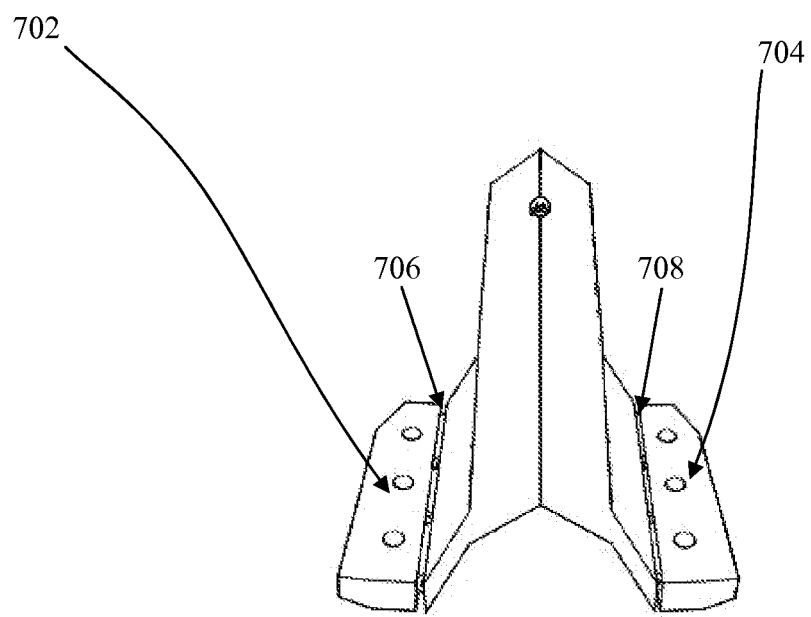

FIG. 10A illustrates a Thoracic/Lumbar TASP-LP with laminar hinged extensions in a neutral position according to an exemplary embodiment (Embodiment II).

Figure 10B:
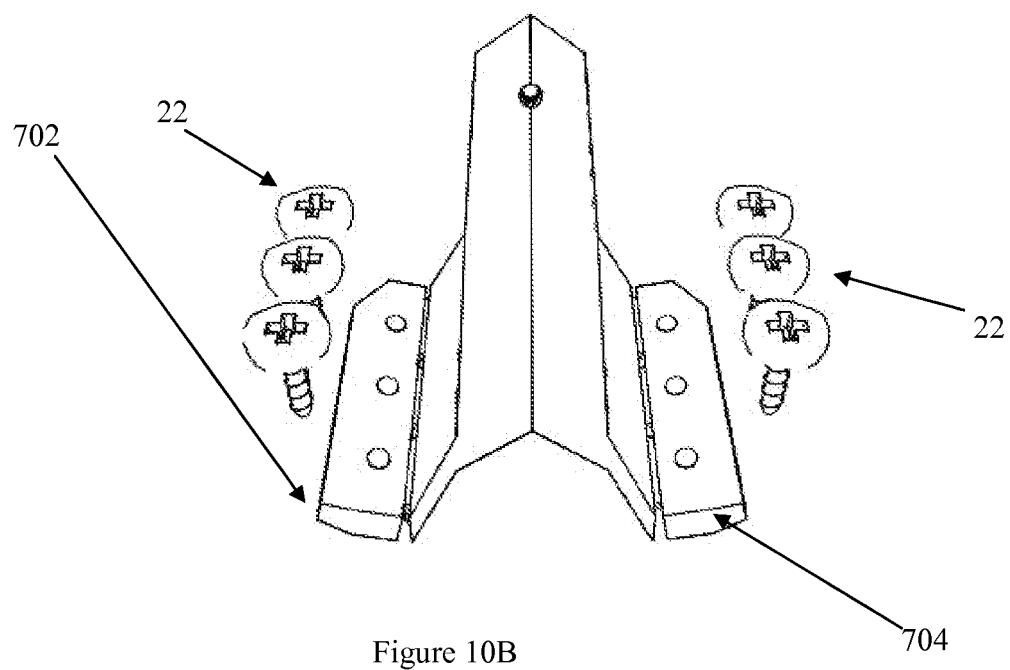

FIG. 10B illustrates a Thoracic/Lumbar TASP-LP with laminar hinged extensions in an elevated position according to an exemplary embodiment (Embodiment II).

Figure 10C:
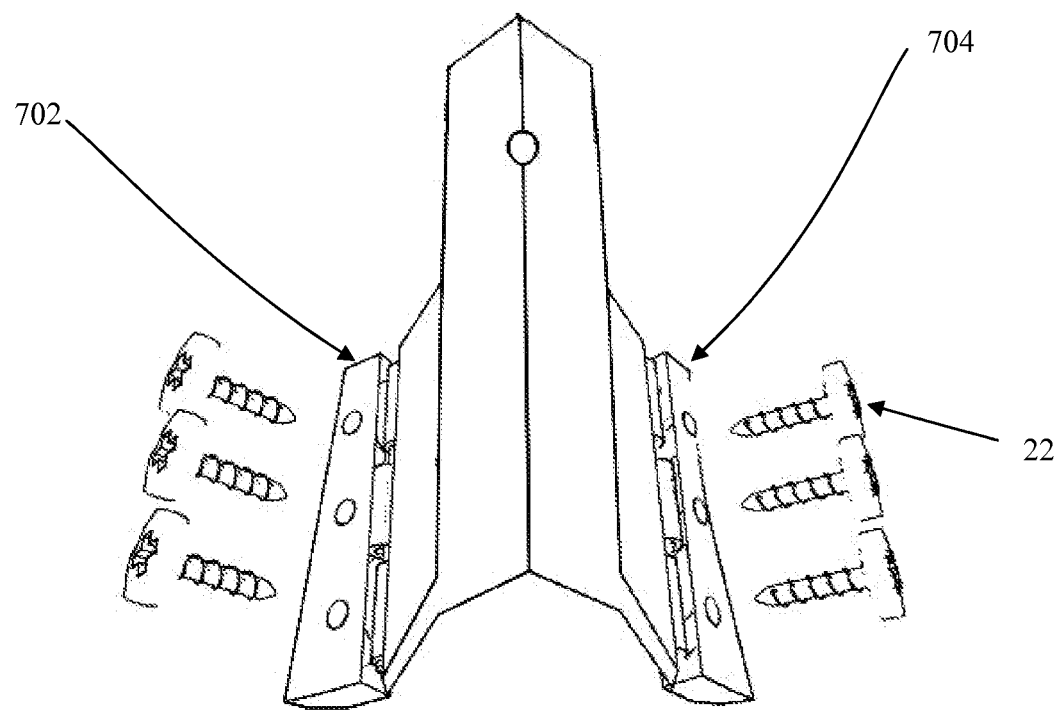

FIG. 10C illustrates a Thoracic/Lumbar TASP-LP with laminar hinged extensions in a depressed position according to an exemplary embodiment (Embodiment II).

Figure 10D:
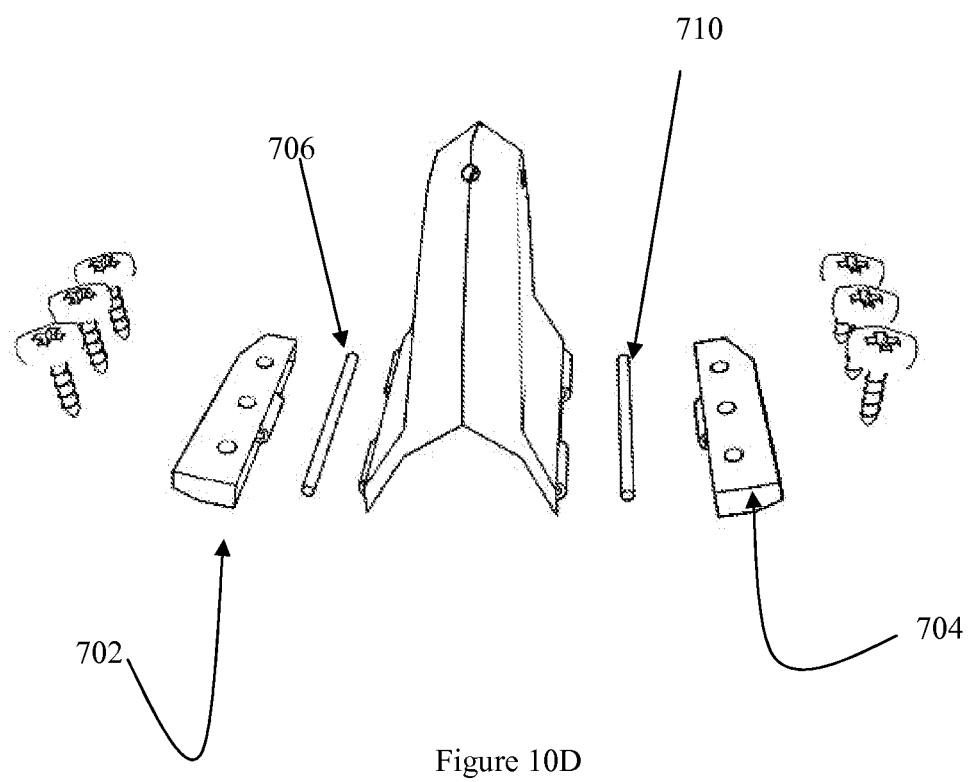

FIG. 10D illustrates an exploded view of the Thoracic/Lumbar TASP-LP according to an exemplary embodiment (Embodiment II).

Figure 11A:
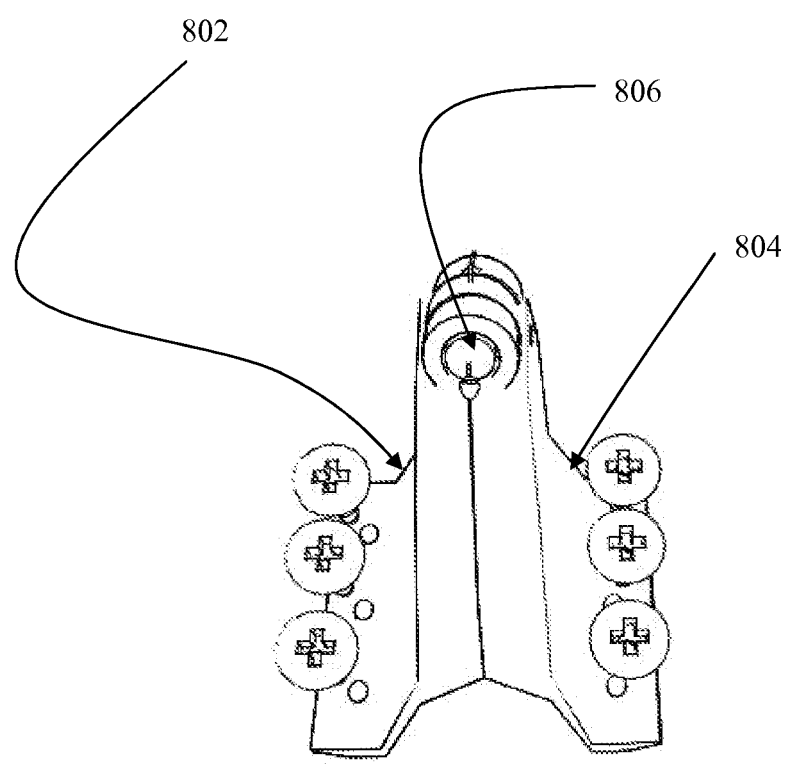

FIG. 11A illustrates a Thoracic-Lumbar TASP-LP with spino-laminar hinged extensions in a neutral position according to an exemplary embodiment (Embodiment III).

Figure 11B:
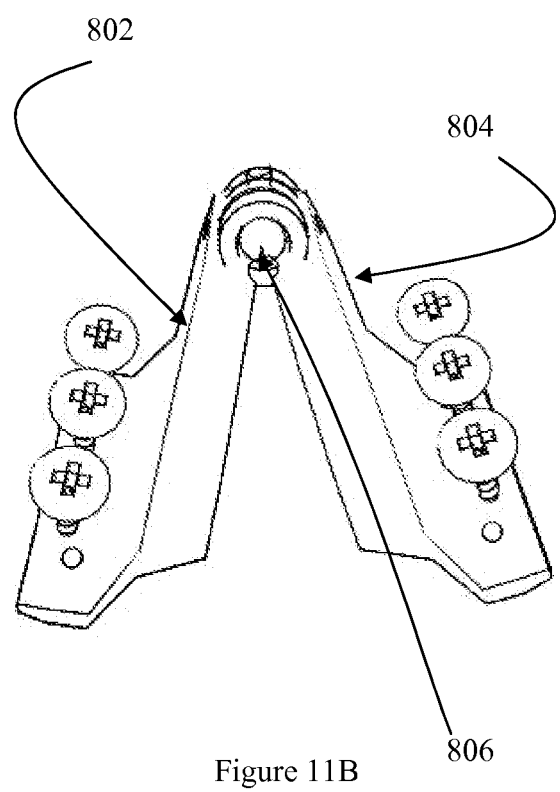

FIG. 11B illustrates a Thoracic-Lumbar TASP-LP with spino-laminar hinged extensions in a slightly elevated position according to an exemplary embodiment (Embodiment III).

Figure 11C:
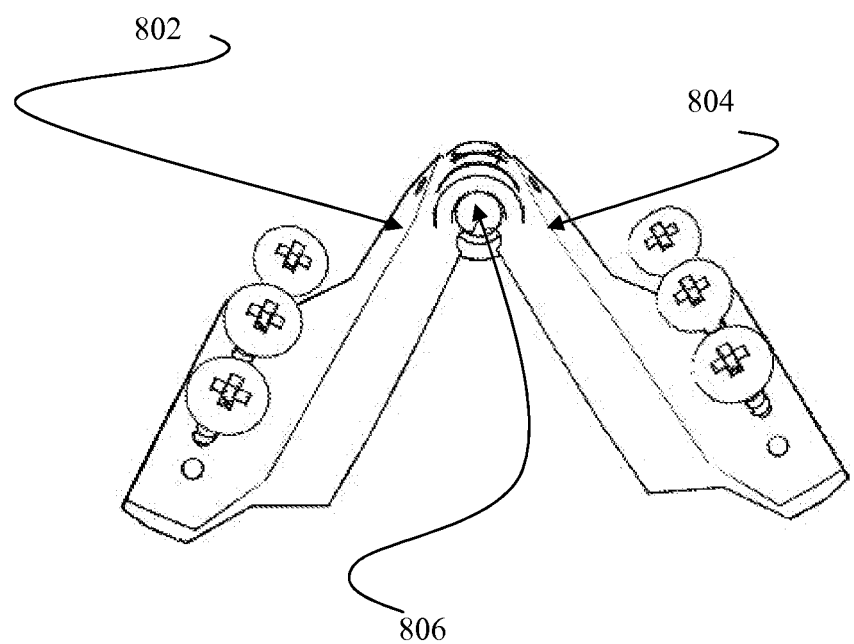

FIG. 11C illustrates a Thoracic-Lumbar TASP-LP with spino-laminar hinged extensions in a markedly elevated position according to an exemplary embodiment (Embodiment III).

Figure 11D:
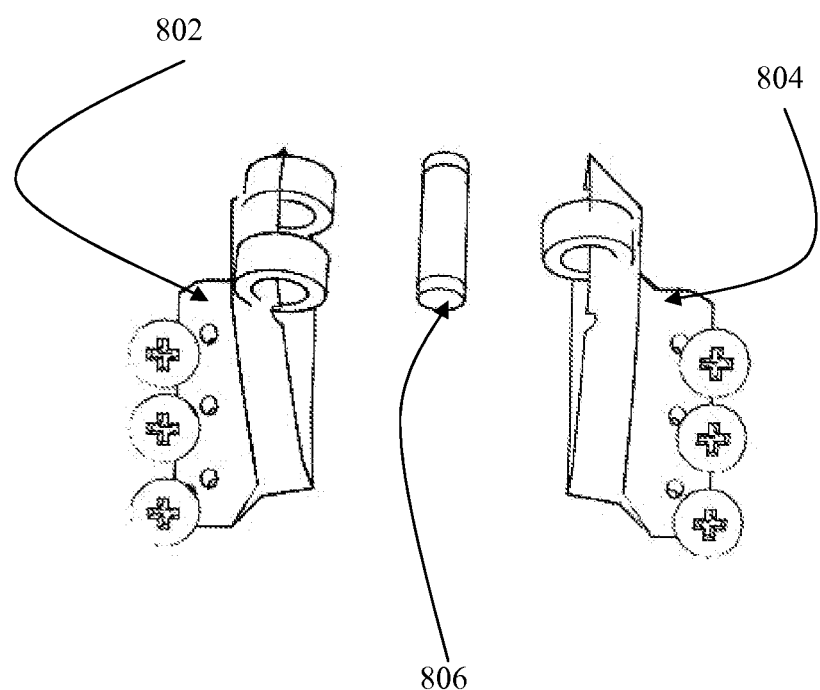

FIG. 11D illustrates an exploded view of the Thoracic-Lumbar TASP-LP according to an exemplary embodiment (Embodiment III).

Figure 12A:
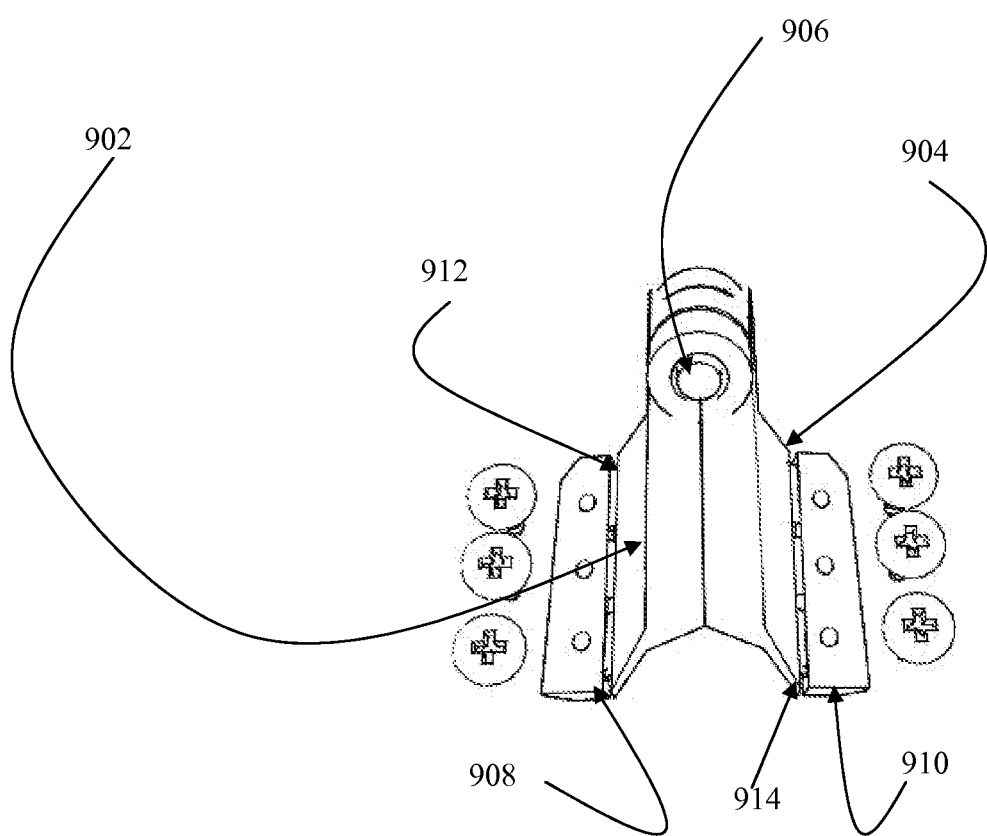

FIG. 12A illustrates an anterior-posterior view of the Thoracic-Lumbar TASP-LP according to an exemplary embodiment (Embodiment IV).

Figure 12B:
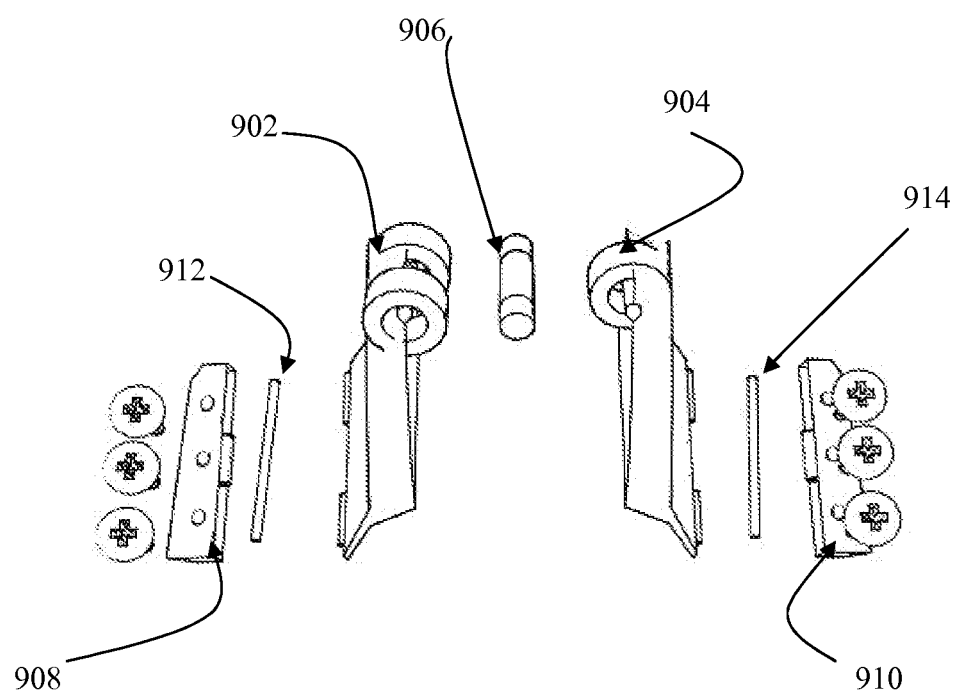

FIG. 12B illustrates an exploded view of the Thoracic-Lumbar TASP-LP according to an exemplary embodiment (Embodiment IV).

DETAILED DESCRIPTION OF THE EXEMPLARY EMBODIMENTS OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Referring now to the drawings, FIGS. 1-12B illustrate exemplary embodiments of a TASP-LP that can solve the aforementioned problems in the cervical, thoracic and lumbar spine by implantation of a TASP-LP into the post-laminectomy spine.

FIGS. 1A-D illustrate a plurality of different views of an exemplary embodiment of a cervical TASP-LP (Embodiment IA) including a single one piece total prosthetic module 10 that can replace a single natural cervical spinous process laminar (left and right) unit.

The total prosthetic module 10 can include, for example, a prosthetic spinous process 12 and left prosthetic lamina 14 and right prosthetic lamina 16. The prosthetic spinous process 12 can include perforations 20 for muscle suture attachment. The left prosthetic lamina 14 and right prosthetic lamina 16 can include screw attachments 18 for receiving translaminar screws 22.

An exemplary embodiment of a cervical TASP-LP construction can be based on a 3-D CT computer rendition which very closely recreates the natural geometric anatomy of the healthy human cervical spine. Hence, an exemplary embodiment of a cervical prosthetic spinous process 12 of the TASP-LP 10 can be bifid (i.e., divided into two lobes), just like the predominant bifid spinous process anatomy of the natural cervical spine 30.

Likewise, using 3-D computer modeling software, in an exemplary embodiment, the slope and angulations of the prosthetic spinous process 12, and of left and right prosthetic lamina 14, 16, can be rendered in accord with the natural spinous process 34 and of left and right natural lamina 30, 32 of the healthy natural cervical spine 30. Hence, as illustrated in the exemplary embodiment of FIG. 1E, when a cervical TASP-LP single module 10 (Embodiment IAi) is implanted into the natural cervical spine 30, the overall shape, height, and spinous process and laminar orientations and angulations of the cervical TASP-LP can mimic the surrounding natural cervical spinous processes 34 and lamina 30, 32 to render the prosthesis almost indistinguishable from the natural cervical spine 30 in which it is embedded.

Figure 1A:
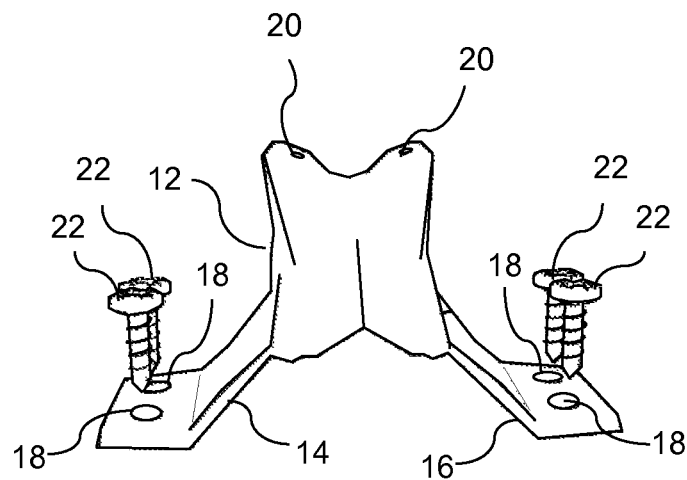
FIG. 1A illustrates an anterior-posterior view of a cervical TASP-LP according to an exemplary embodiment (Embodiment IAi).
Figure 1B:
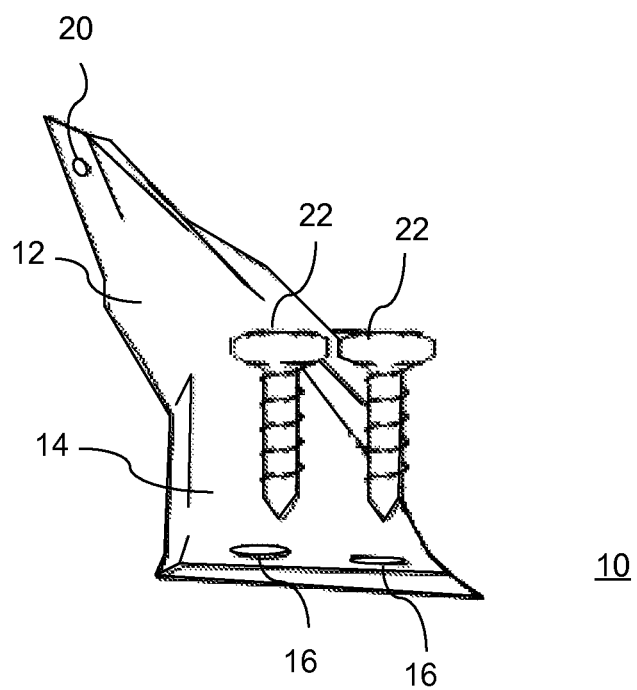
FIG. 1B illustrates a lateral view of a cervical TASP-LP according to an exemplary embodiment (Embodiment IAi).
Figure 1C:
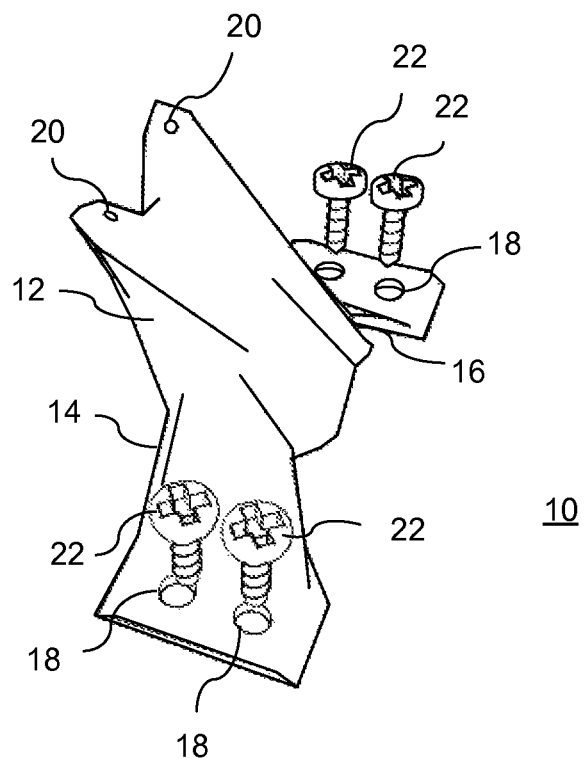
FIG. 1C illustrates an oblique view of a cervical TASP-LP according to an exemplary embodiment (Embodiment IAi).
Figure 1D:
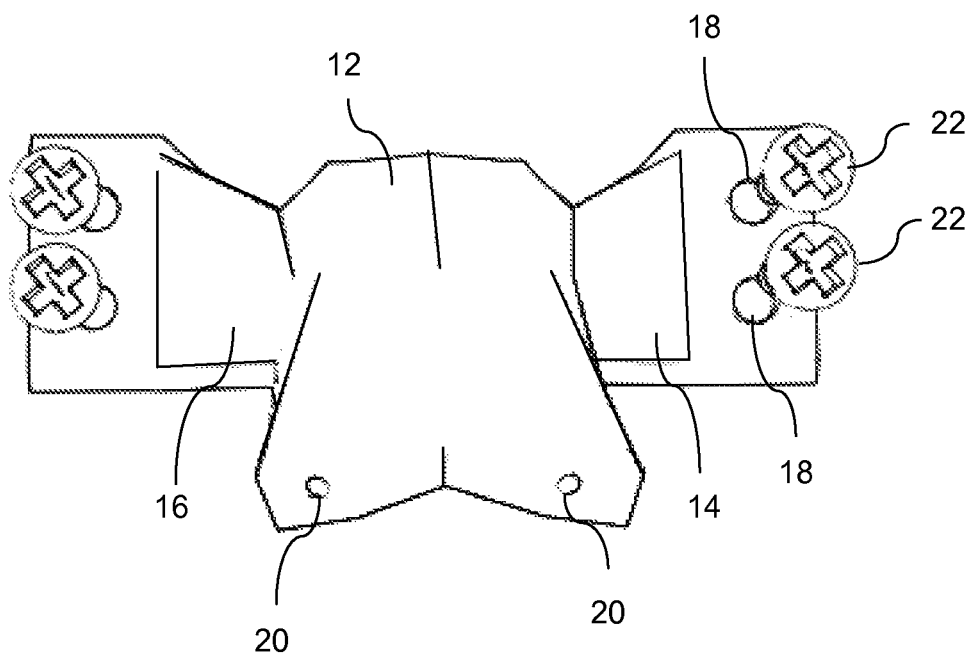
FIG. 1D illustrates a superior view of a cervical TASP-LP according to an exemplary embodiment (Embodiment IAi).
Figure 1E:
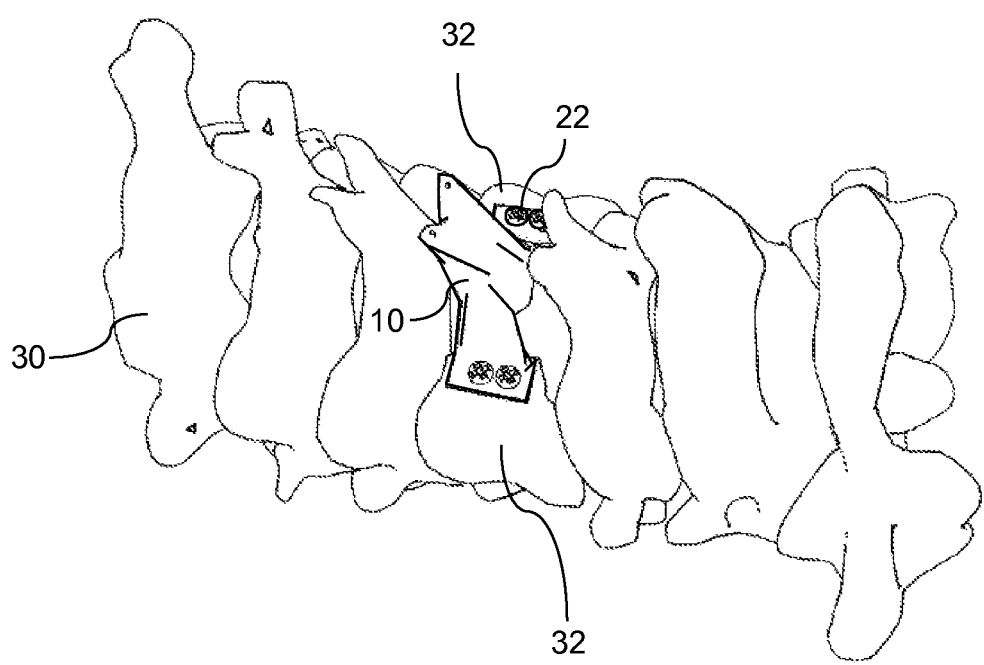
FIG. 1E illustrates a superior-implanted view of a cervical TASP-LP according to an exemplary embodiment (Embodiment IAi).
Figure 1F:
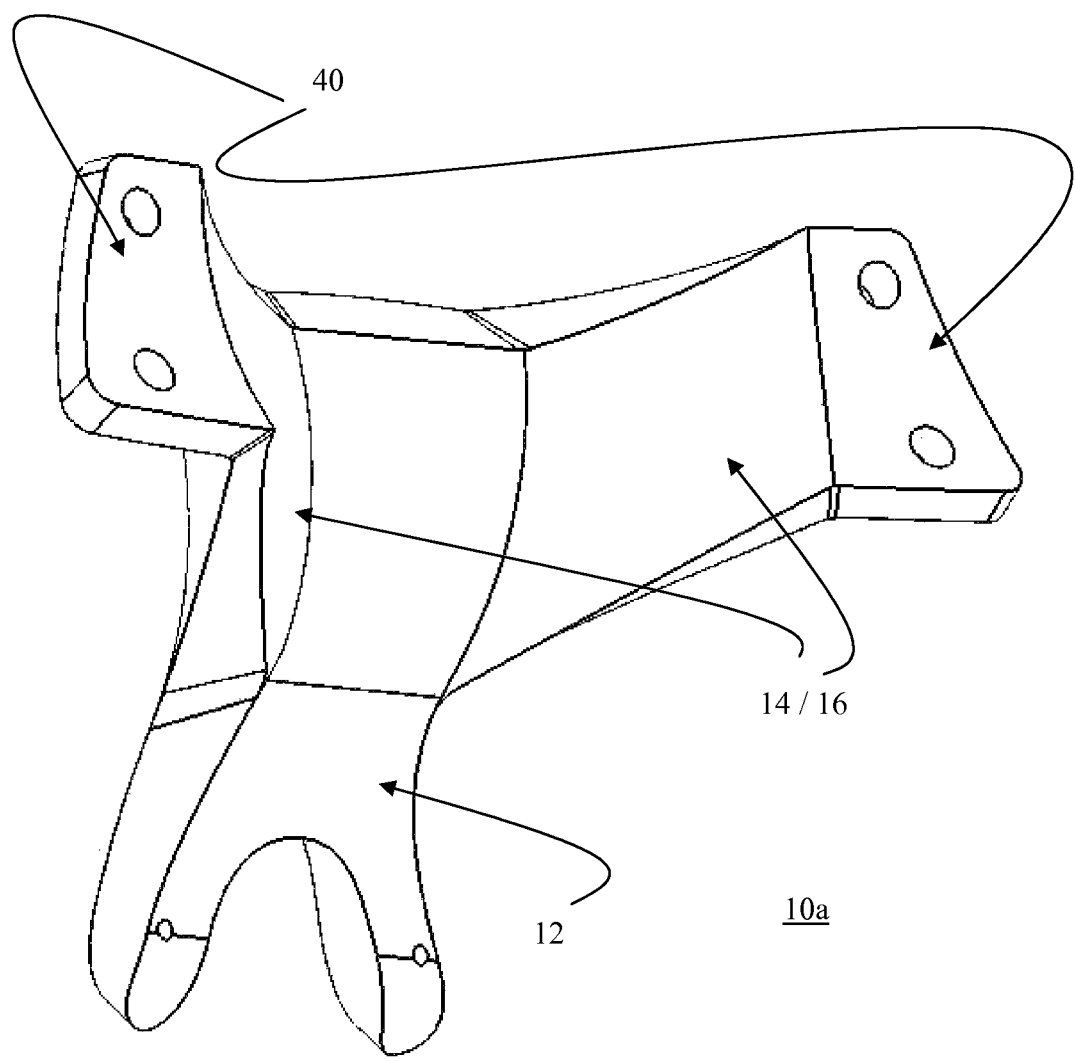
FIG. 1F illustrates an inferior-oblique view of a cervical TASP-LP according to an exemplary embodiment (Embodiment IAii).

With reference to FIG. 1F, an exemplary embodiment of a slightly different singular module 10a (Embodiment IAii) will now be described in which the undersurfaces of the laminar mounting surfaces 40 can be contoured to approximate the shape of the underlying cervical lamina (e.g., 30, 32) to which the prosthesis 10a is mounted.

Figure 1G:
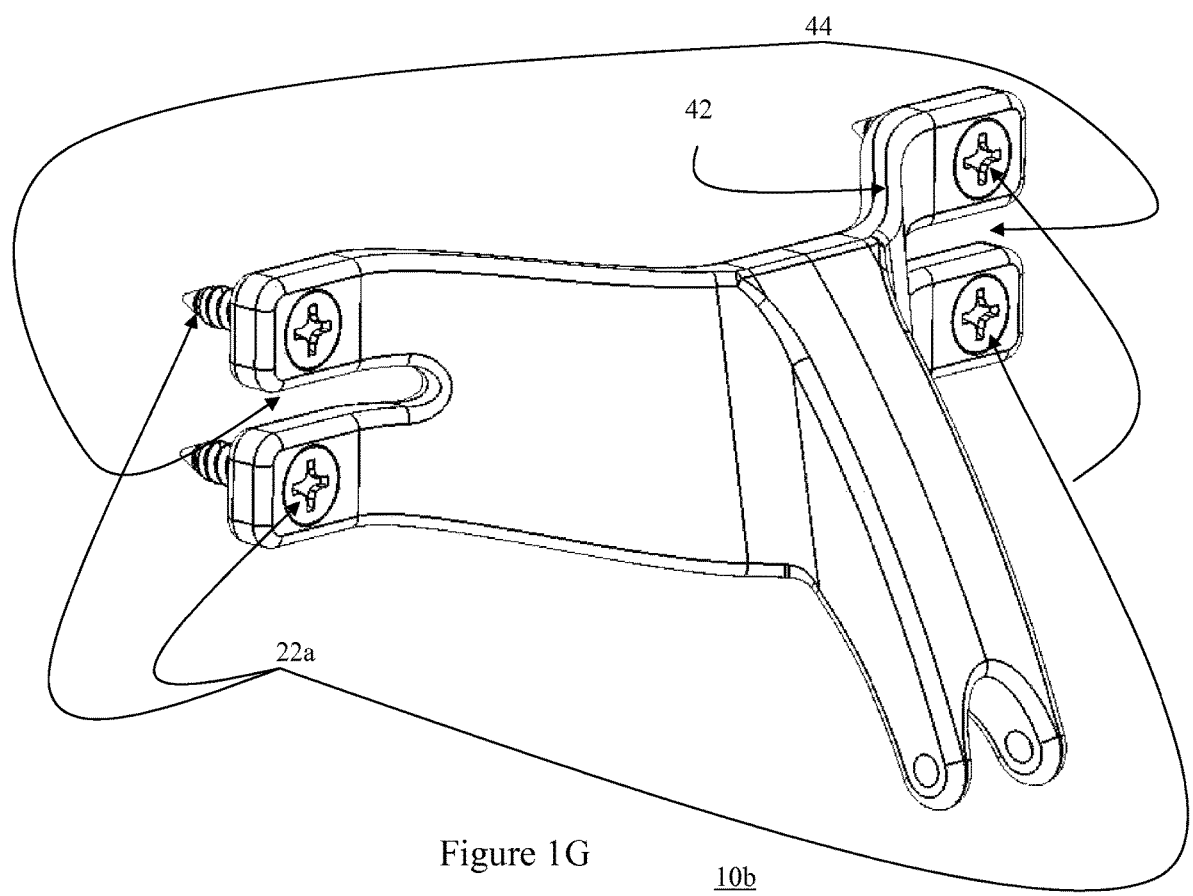
FIG. 1G illustrates a top view of a cervical TASP-LP according to an exemplary embodiment (Embodiment IAiii).
Figure 1H:
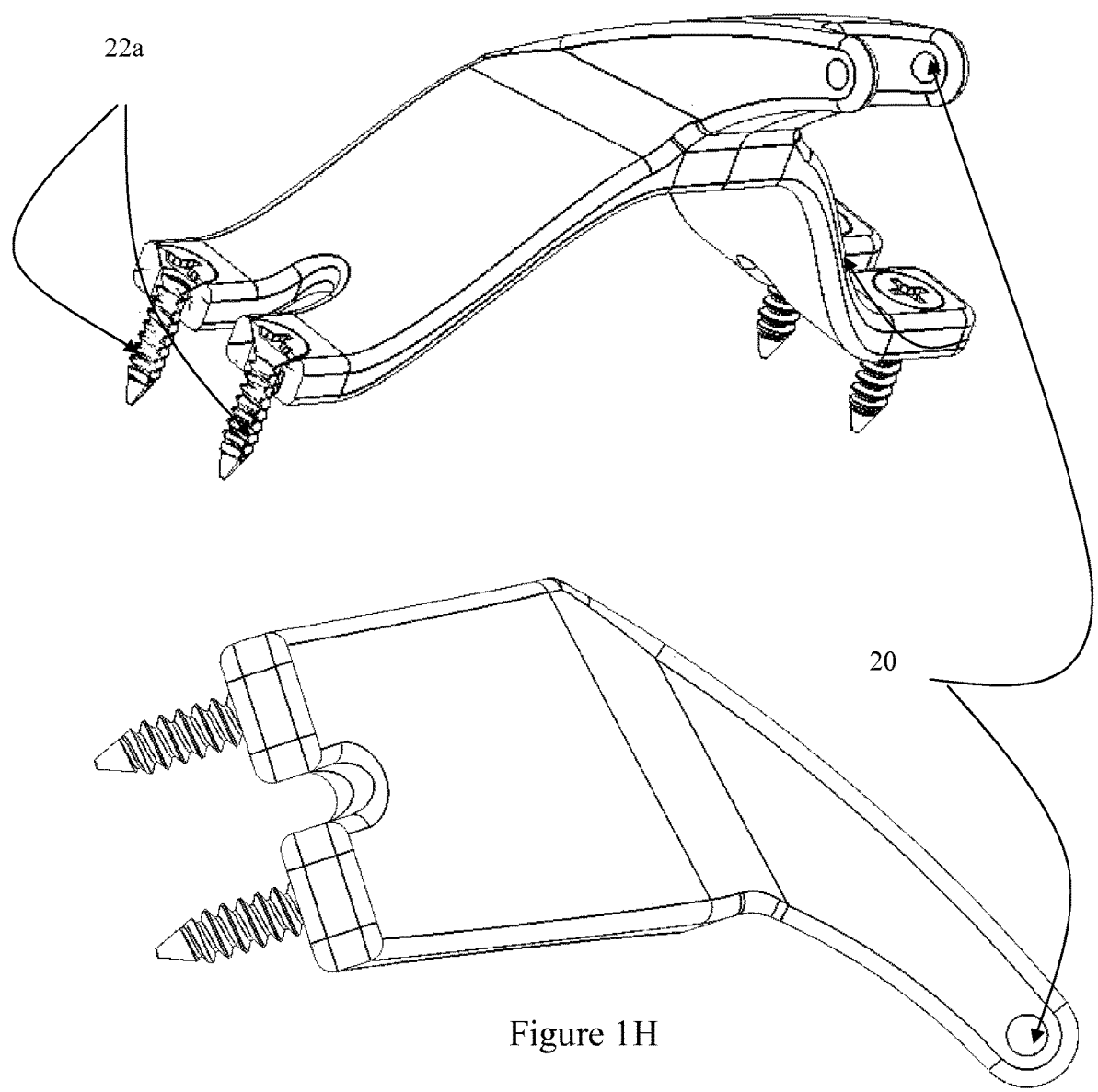
FIG. 1H illustrates an oblique view and a side view of a cervical TASP-LP according to an exemplary embodiment (Embodiment IAiii).

FIGS. 1G-H illustrate yet another exemplary embodiment of the single module 10b (Embodiment IAiii) including a relief (e.g., laminar mounting relief 44) added on each side that enables slight flexing for mounting. In addition, the prosthetic lamina 14, 16 can be thinned (e.g., thinned laminar section 42) to thereby also allow slightly more flexibility. The features of the exemplary embodiment can be facilitated by producing the exemplary prosthesis 10b using titanium or similar bio-compatible materials.

FIG. 1H illustrates a cross-sectional view of an exemplary embodiment that demonstrates that flat screw heads (e.g., flat head mounting trans-laminar screws 22a) can be countersunk into the surface, whereby the screws 22a are, for example, locked into position.

The exemplary embodiments of the prosthetic spinous process 12 can include perforations 20 on either side of the bifid process 12 to enable suturing of cervical muscles and fascia to the prosthetic spinous process 12, to reconstruct the normal cervical muscular architecture. The left and right prosthetic lamina 14, 16 can include, for example, two perforations 18 on its extensions, thereby enabling the fixation of the TASP-LP to the natural lamina (FIG. 1E) by translaminar screws 22a.

Figure 2A:
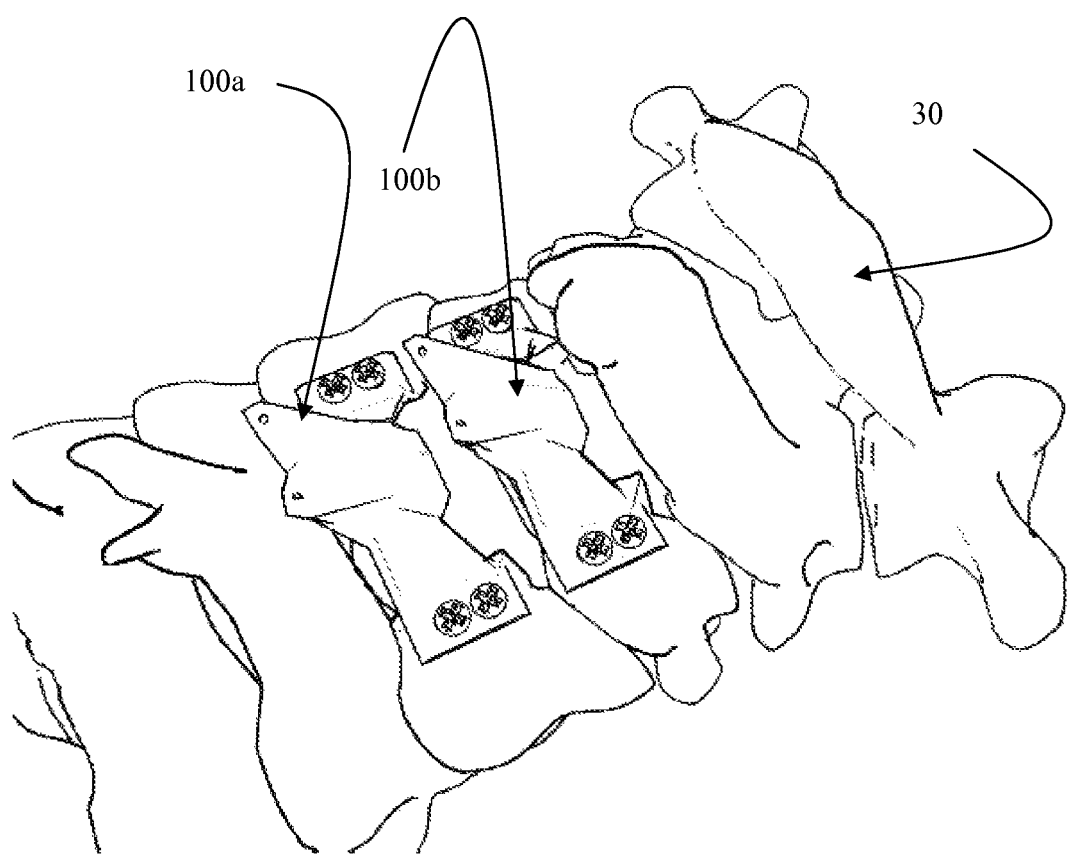
FIG. 2A illustrates the implantation of two (A) cervical TASP-LP modules into the cervical spine according to an exemplary embodiment (Embodiment IA).
Figure 2B:
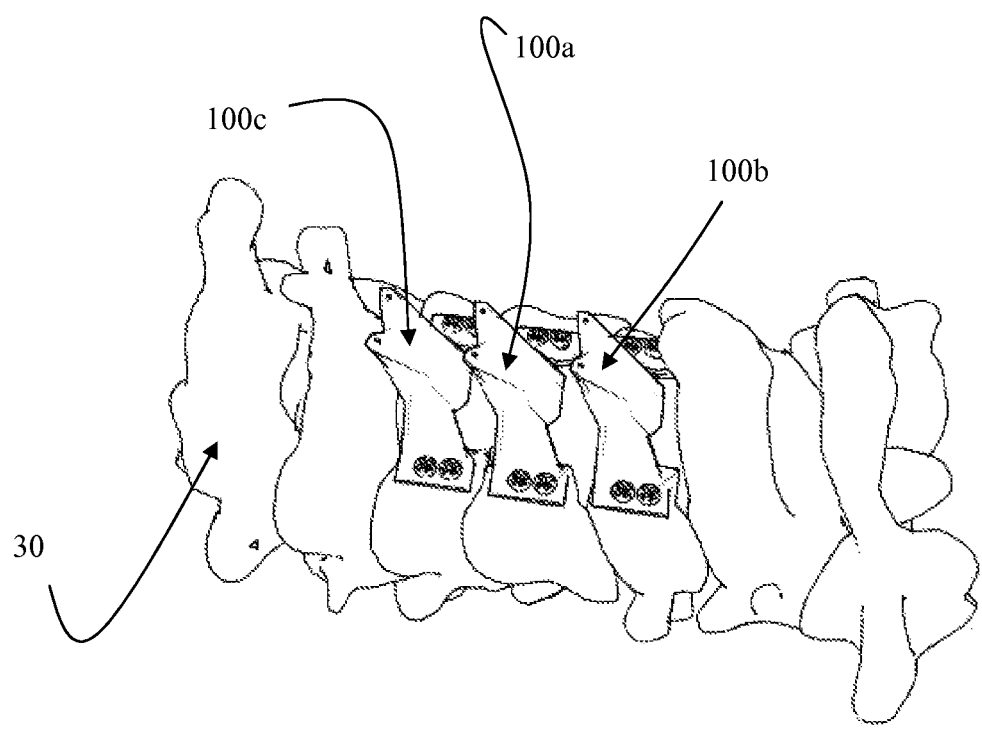
FIG. 2B illustrates the implantation of three (B) cervical TASP-LP modules into the cervical spine according to an exemplary embodiment (Embodiment IA).

FIGS. 2A and 2B illustrate an exemplary embodiment of a cervical TASP-LP 100 (embodiment IA) that can be modularly applied to two and three level multi-level laminectomies. Other exemplary embodiments can likewise be applied to four, five, etc. multi-level laminectomies in a modular manner.

FIG. 2A illustrates an exemplary embodiment in which a TASP-LP module 100a (module #1), and module 100b (module #2) are inserted into a 2 level post-laminectomy natural cervical spine 30. FIG. 2B illustrates an exemplary embodiment in which TASP-LP modules 100a, 100b, 100c (modules #1, #2, and #3) are inserted into a 3-level post-laminectomy natural cervical spine 30. In both FIGS. 2A and 2B, the prosthetic modules 100a, 100b, 100c can reproduce and artificially reconstruct the natural geometry of the healthy human spine 30.

In other exemplary embodiments, the different modules can be manufactured in different heights, lengths, and widths so that the surgeon can select from the properly sized one to integrate with the selective anatomy of different patients.

Figure 3A:
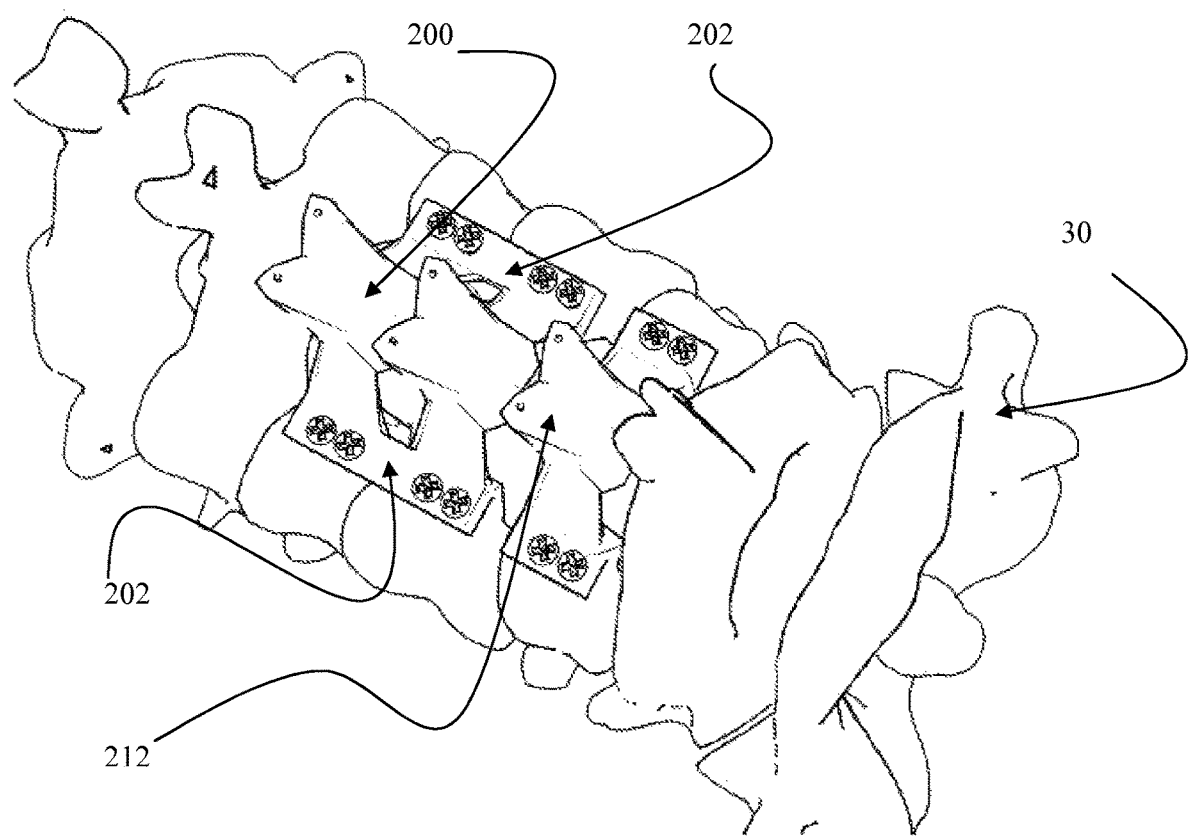
FIG. 3A illustrates a superior-oblique view of a double TASP-LP according to an exemplary embodiment (Embodiment IB) inserted into the cervical spine and a hybrid of double (Embodiment IB) and single TASP-LP according to an exemplary embodiment (Embodiment IA) modules inserted into the cervical spine.
Figure 3B:
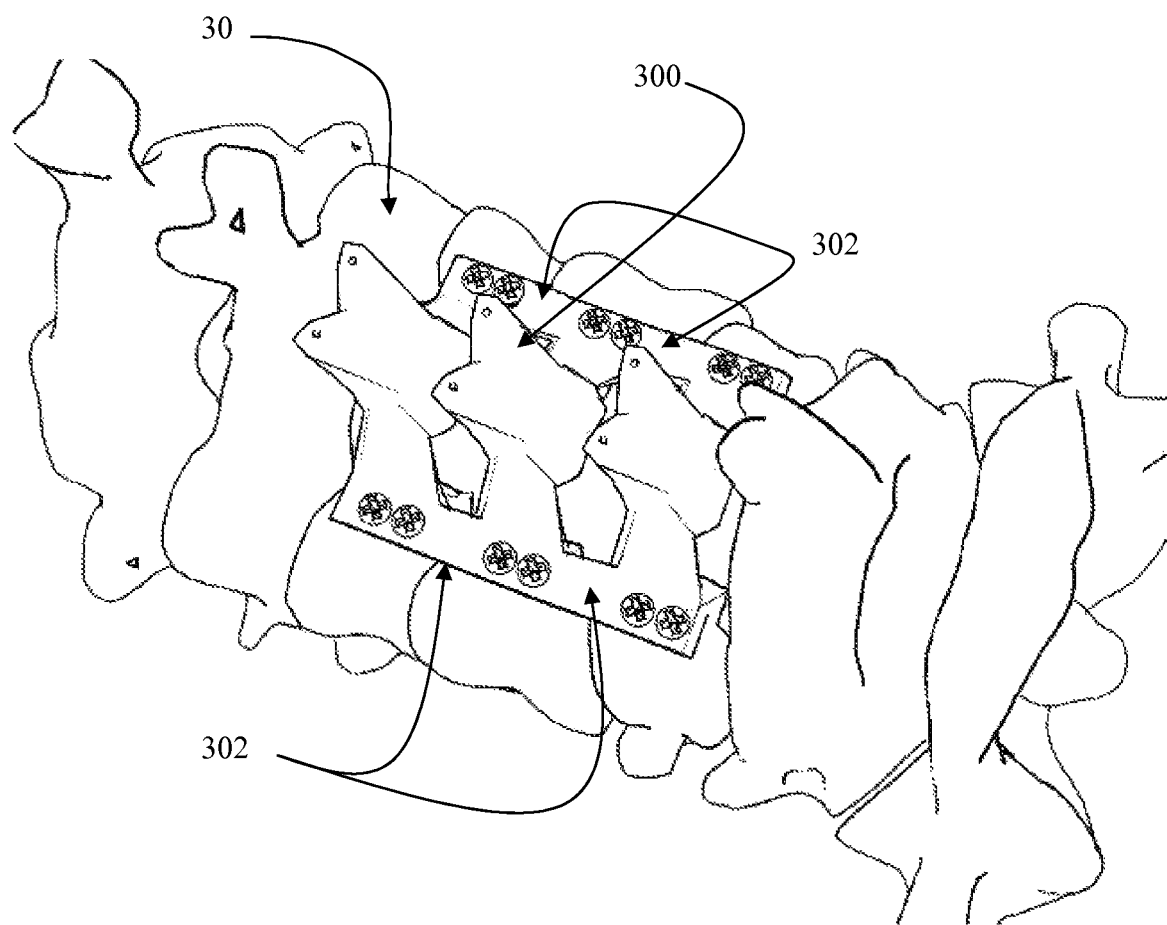
FIG. 3B illustrates a triple cervical TASP-LP module according to an exemplary embodiment (Embodiment IC) inserted into the cervical spine.

FIGS. 3A and 3B illustrate other exemplary embodiment (Embodiments IB and IC), respectively.

FIG. 3A illustrates an exemplary embodiment (Embodiment IB) including a double spinous process-laminar prosthetic unit 200. The prosthetic unit 200 can be a single piece and can be similar to the single module TASP-LP (Embodiment IA, e.g., 10, 10a, 100a, 100b, 100c). However, in the illustrated embodiment, the prosthetic unit 200 can include two modules unified (e.g., integrally formed) into one piece with modular laminar connecting bridges 202 on the left and right sides of the prosthesis 200. Thus, FIG. 3A shows the implantation of a double spinous process-laminar prosthetic module 200 (Embodiment IB) and a single spinous-laminar prosthetic module (embodiment IA, e.g., 10) into a 3-level post-laminectomy cervical spine 30. This is essentially a hybrid reconstruction. The surgeon can choose to replace three natural units with either 3 single TASP-LP modules (Embodiment IA, e.g., 10), or with a combination of a double TASP-LP module 200 (Embodiment IB) and a single TASP-LP module (Embodiment IA, e.g., 10), or with a single Triple TASP-LP module (embodiment IC, e.g., 100a, 100b, 100c) as illustrated, for example, in FIG. 3B. This triple embodiment 300 (FIG. 3B) can include three modules fused, or integrally formed, into one using two modular connecting bridges 302 on the right and left sides of the module 300.

FIGS. 4A-D illustrate a plurality of different views of an exemplary embodiment of a Thoracic/Lumbar TASP-LP 10 (Embodiment IAi). The Thoracic/Lumbar TASP-LP can be a single one piece total prosthetic module 10 which replaces a single natural Thoracic/Lumbar spinous process-laminar (left and right) unit based on, for example, 3-D CT computer modeling, and can very closely reproduce the normal anatomy of the Thoracic/Lumbar spine. Hence, the exemplary prosthetic spinous process 12 can be monofid, just like the natural anatomy for the majority of the Thoracic and Lumbar spinal elements. The slope and angulations of the exemplary prosthetic spinous process 12, and of the left and right prosthetic lamina 14, 16 can be rendered in accord with the normal Thoracic/Lumbar anatomy using 3-D computer modeling technology. Hence, as illustrated in FIG. 1E, when the Thoracic/Lumbar TASP-LP single module (Embodiment IAi) is implanted into the natural Lumbar spine, the overall shape, height, and the spinous process 12 and laminar orientations and angulations of the prosthesis can mimic the surrounding natural Lumbar spinous processes and lamina, rendering the prosthesis 10 almost indistinguishable from the natural Lumbar spine in which it is embedded.

An exemplary prosthetic spinous process 12 can include perforations to enable suturing of Thoracic/Lumbar muscles and fascia to the prosthesis, to reconstruct the normal muscle orientation and architecture. The left and right prosthetic lamina can include, for example, three perforations on its extensions, which can enable the fixation of the TASP-LP to the natural lamina by trans-laminar screws as exemplarily illustrated in FIG. 4E.

Figure 4A:
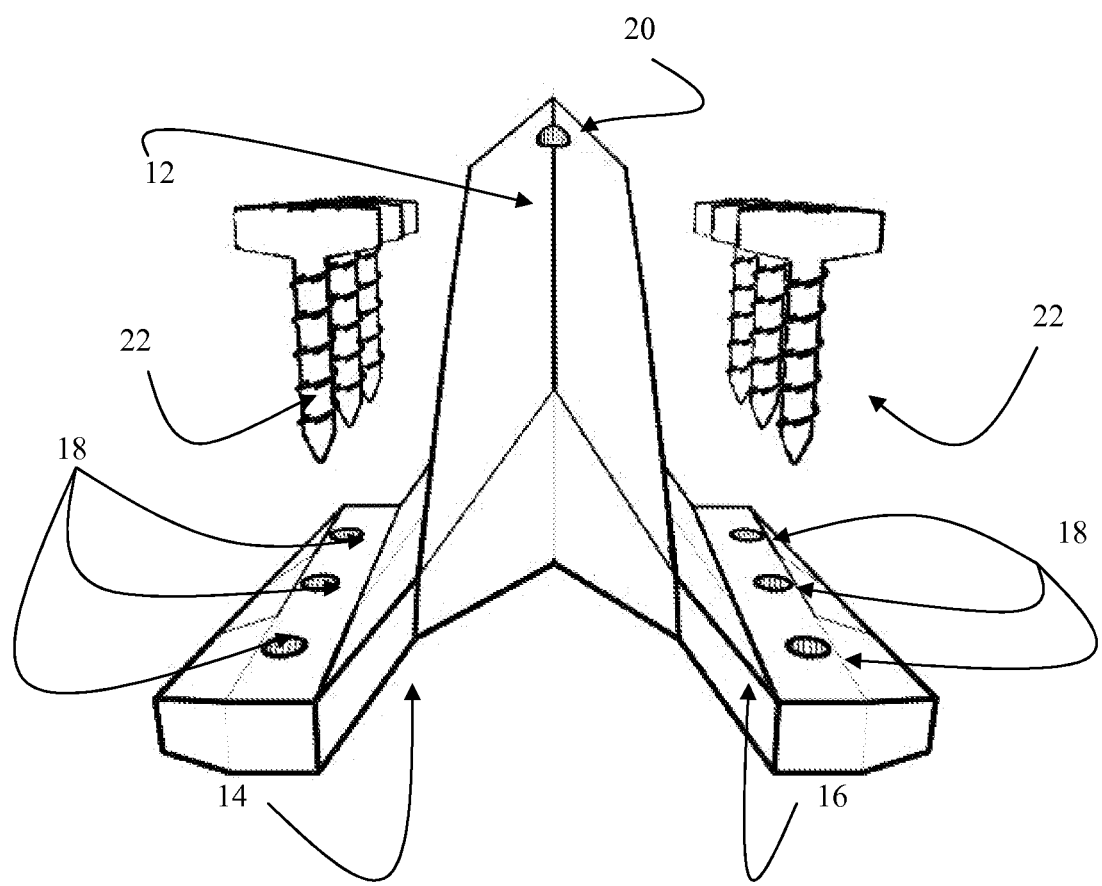
FIG. 4A illustrates an anterior-posterior view of the Thoracic/Lumbar TASP-LP according to an exemplary embodiment (Embodiment IAi).
Figure 4B:
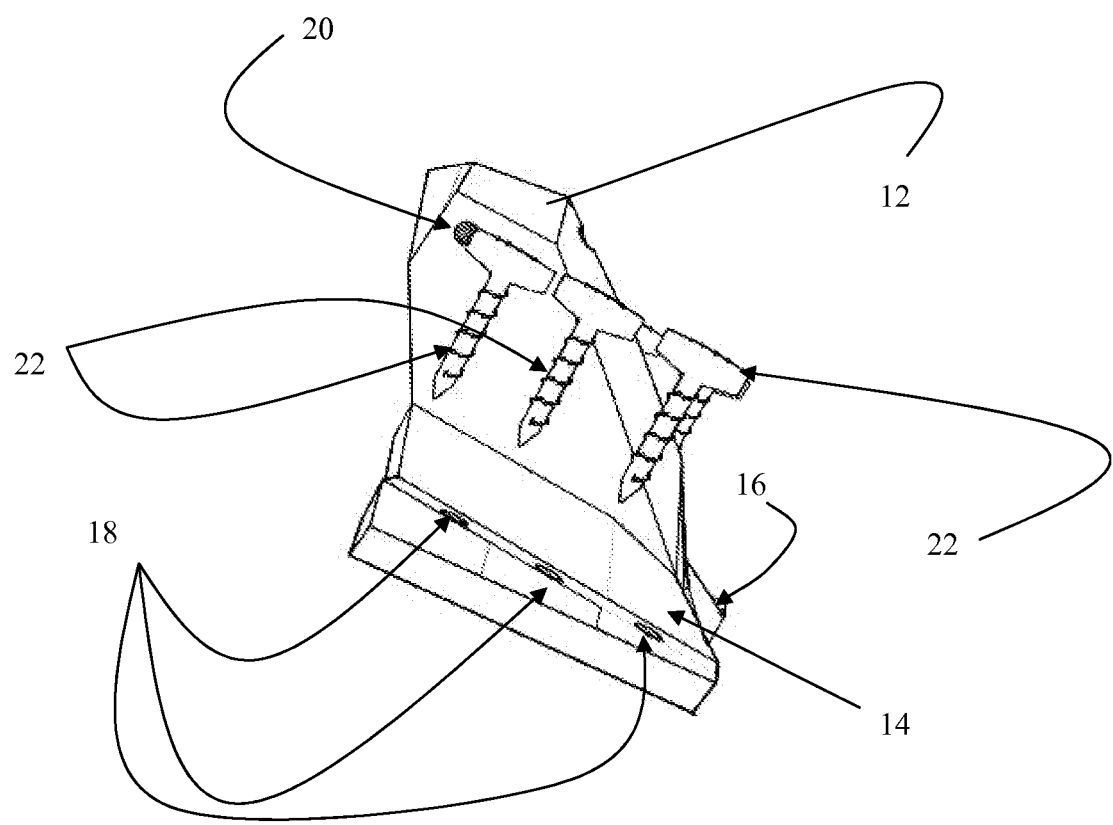
FIG. 4B illustrates a lateral view of the Thoracic/Lumbar TASP-LP according to an exemplary embodiment (Embodiment IAi).
Figure 4C:
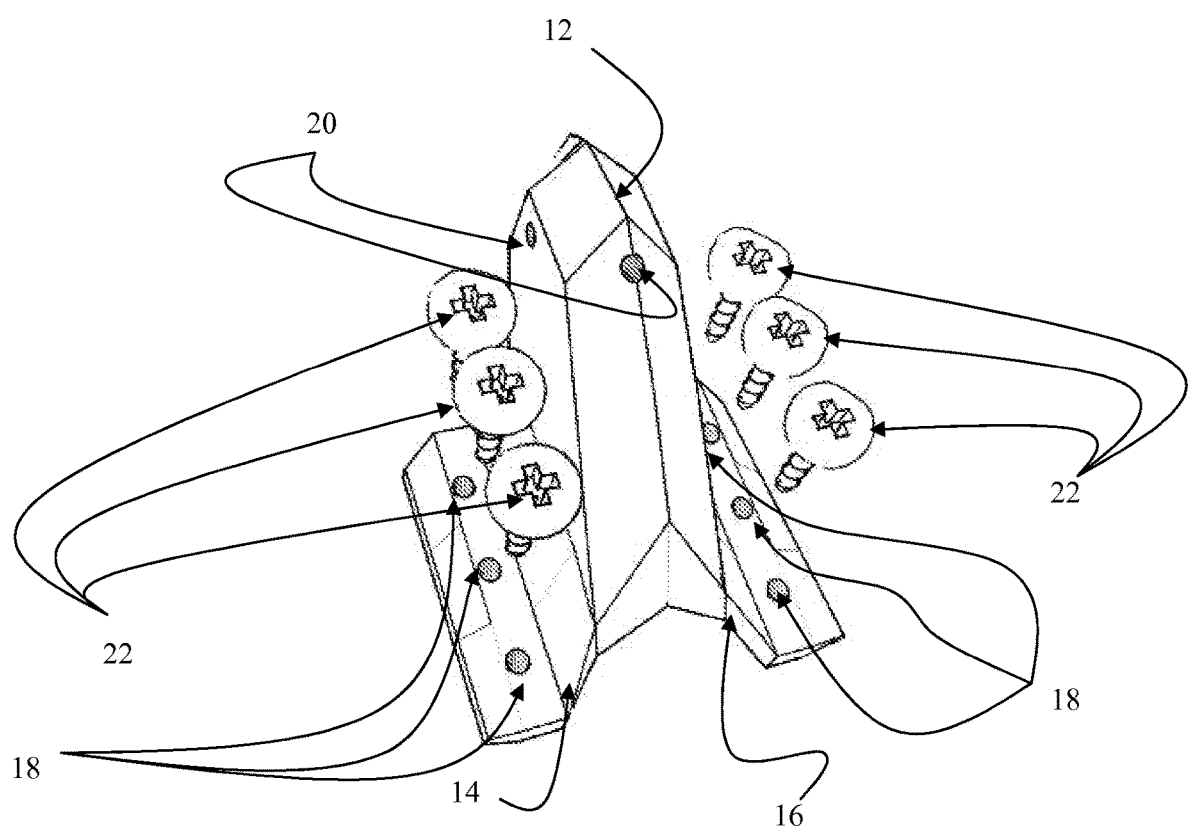
FIG. 4C illustrates an oblique view of the Thoracic/Lumbar TASP-LP according to an exemplary embodiment (Embodiment IAi).
Figure 4D:
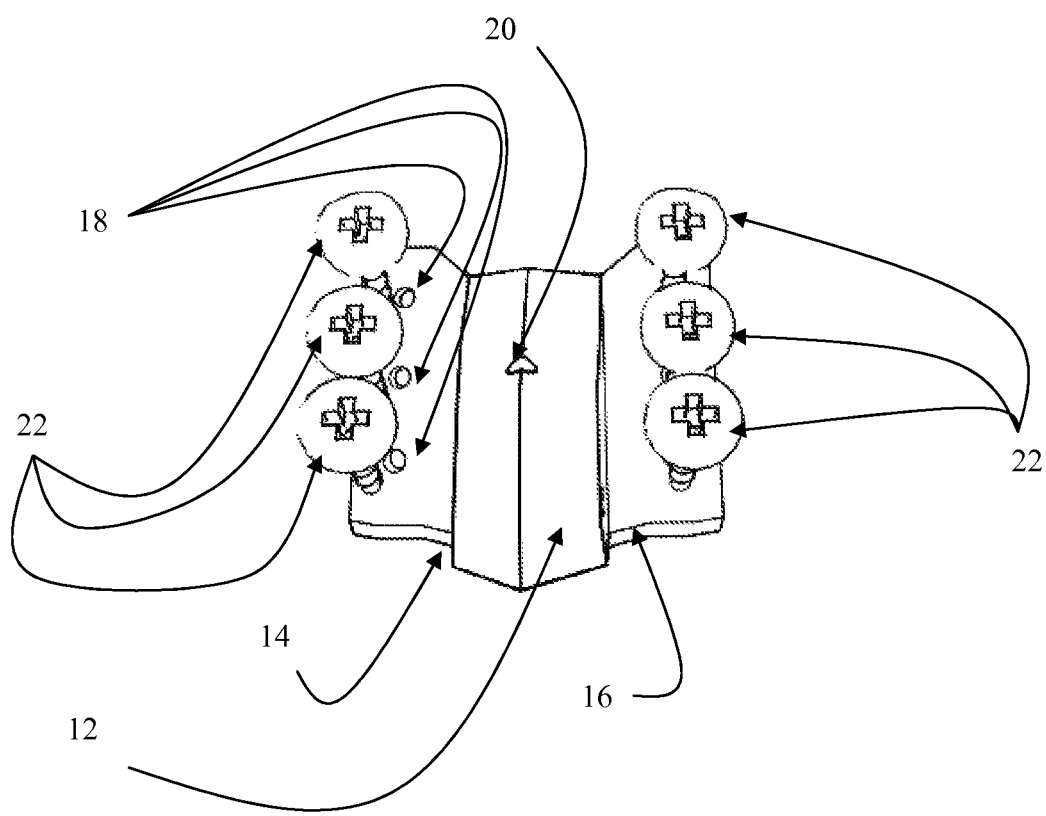
FIG. 4D illustrates a superior view of the Thoracic/Lumbar TASP-LP according to an exemplary embodiment (Embodiment IAi).
Figure 4E:
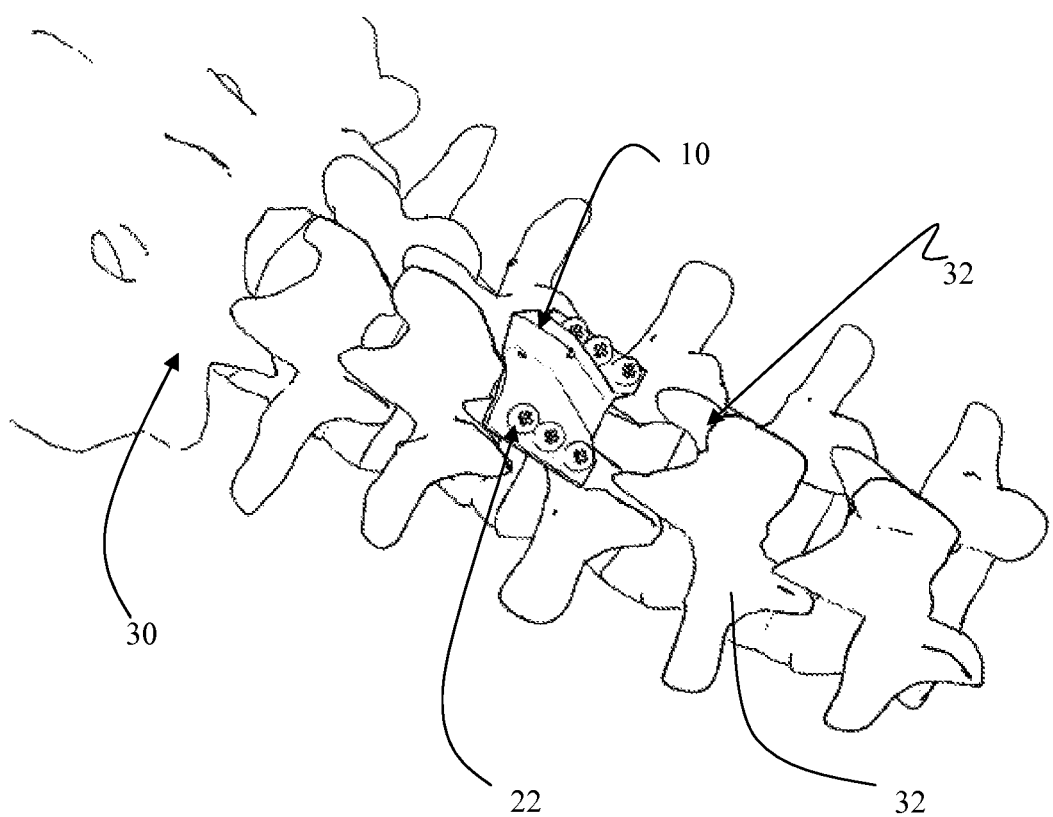
FIG. 4E illustrates a superior implanted view of the Thoracic/Lumbar TASP-LP according to an exemplary embodiment (Embodiment IAi).
Figure 4F:
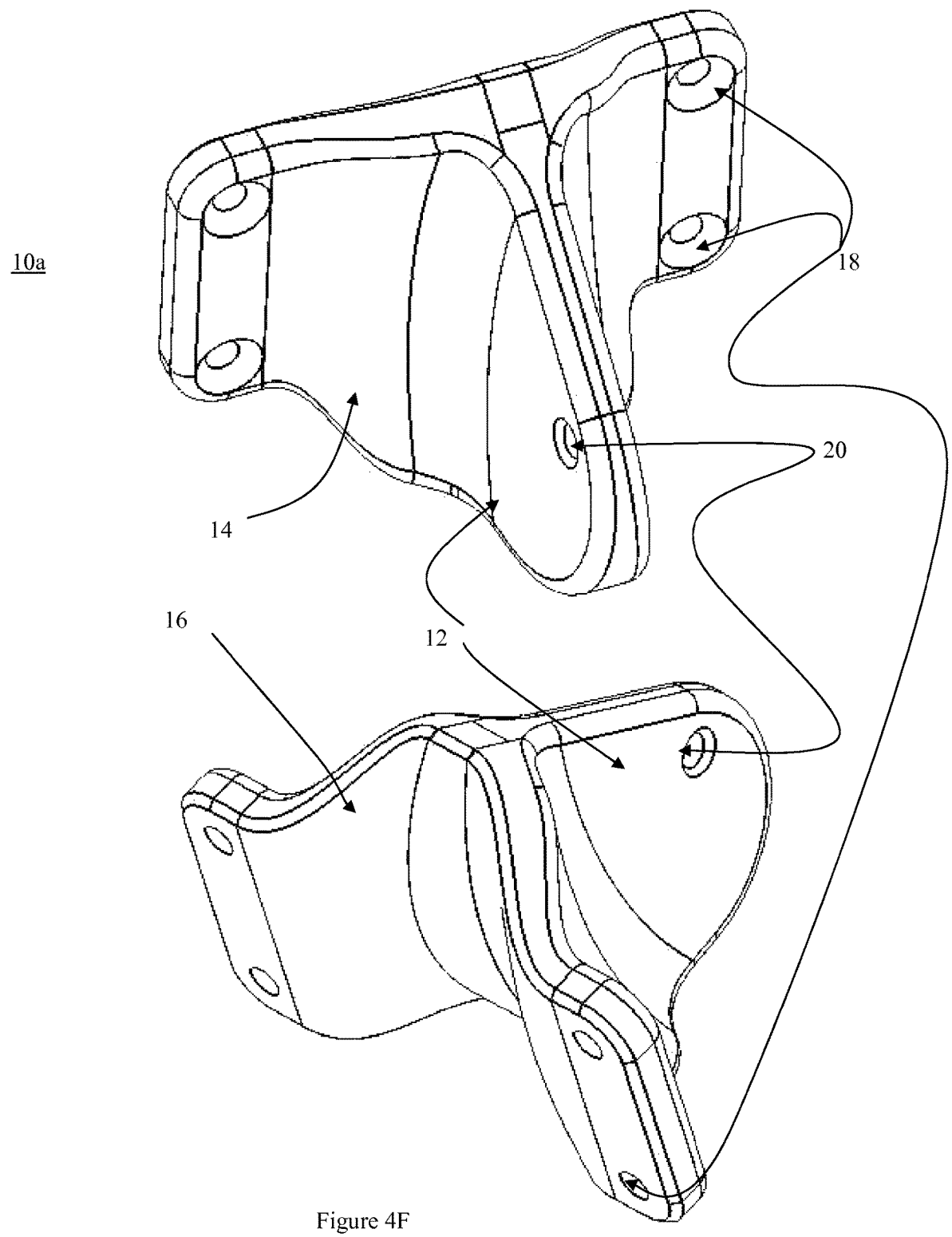
FIG. 4F illustrates a superior and inferior-oblique view of the Thoracic/Lumbar TASP-LP according to an exemplary embodiment (Embodiment IAii).

FIG. 4F illustrates another exemplary embodiment of a single modular Lumbar-Thoracic TASP-LP 10a (Embodiment IAii) wherein the prosthesis 10a can include a different contour and two perforations 18 (instead of three perforations) on either side for trans-laminar screw mounting.

Figure 4G:
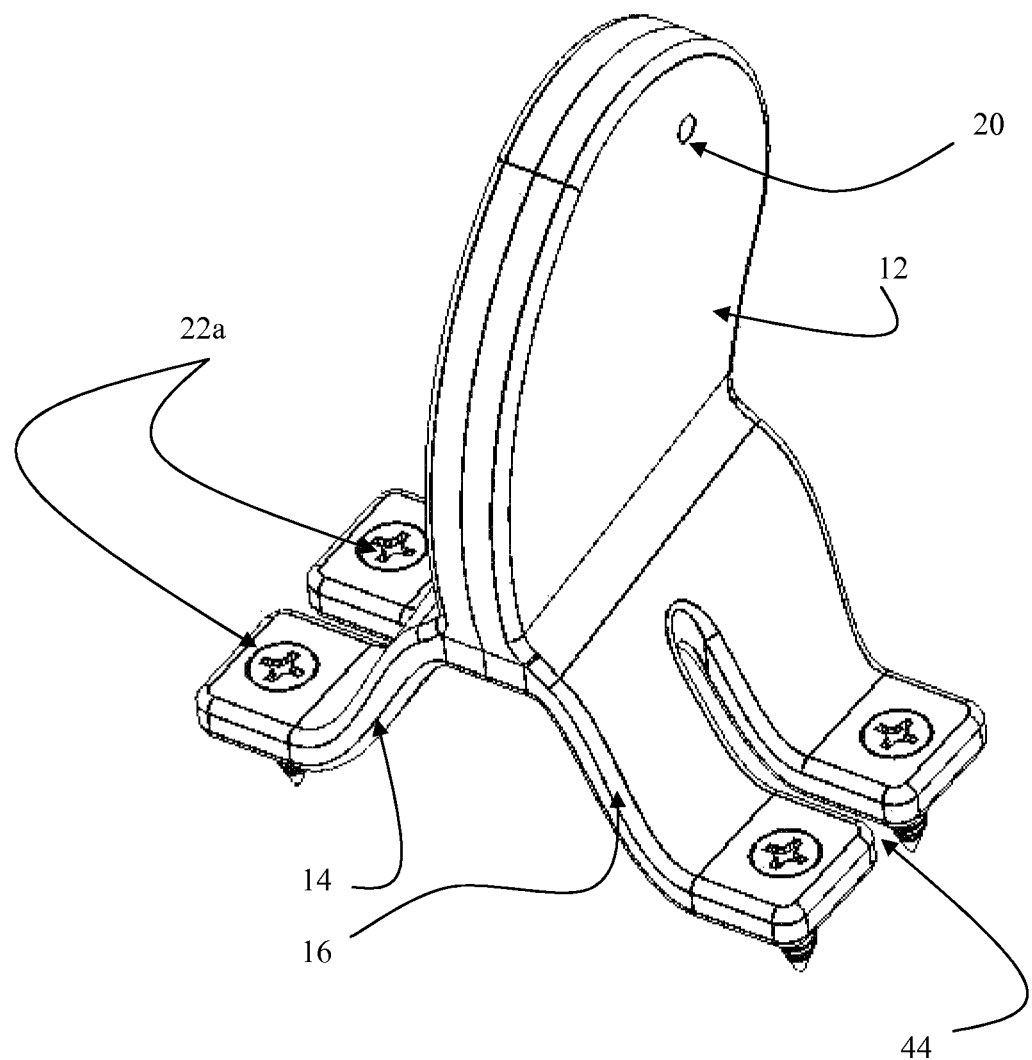
FIG. 4G illustrates a top view of the Thoracic/Lumbar TASP-LP according to an exemplary embodiment (Embodiment IAiii).

FIG. 4G illustrates yet another exemplary embodiment of a single modular Lumbar/Thoracic TASP-LP 10a (Embodiment IAiii) wherein a relief 44 can be added on each side to make the prosthesis somewhat more malleable and flexible. Similarly, the prosthetic laminar edges can be somewhat more thinned out for the sake of increased malleability. These features may be more amenable to production of the prosthesis in titanium or any biocompatible material with similar properties.

Figure 5A:
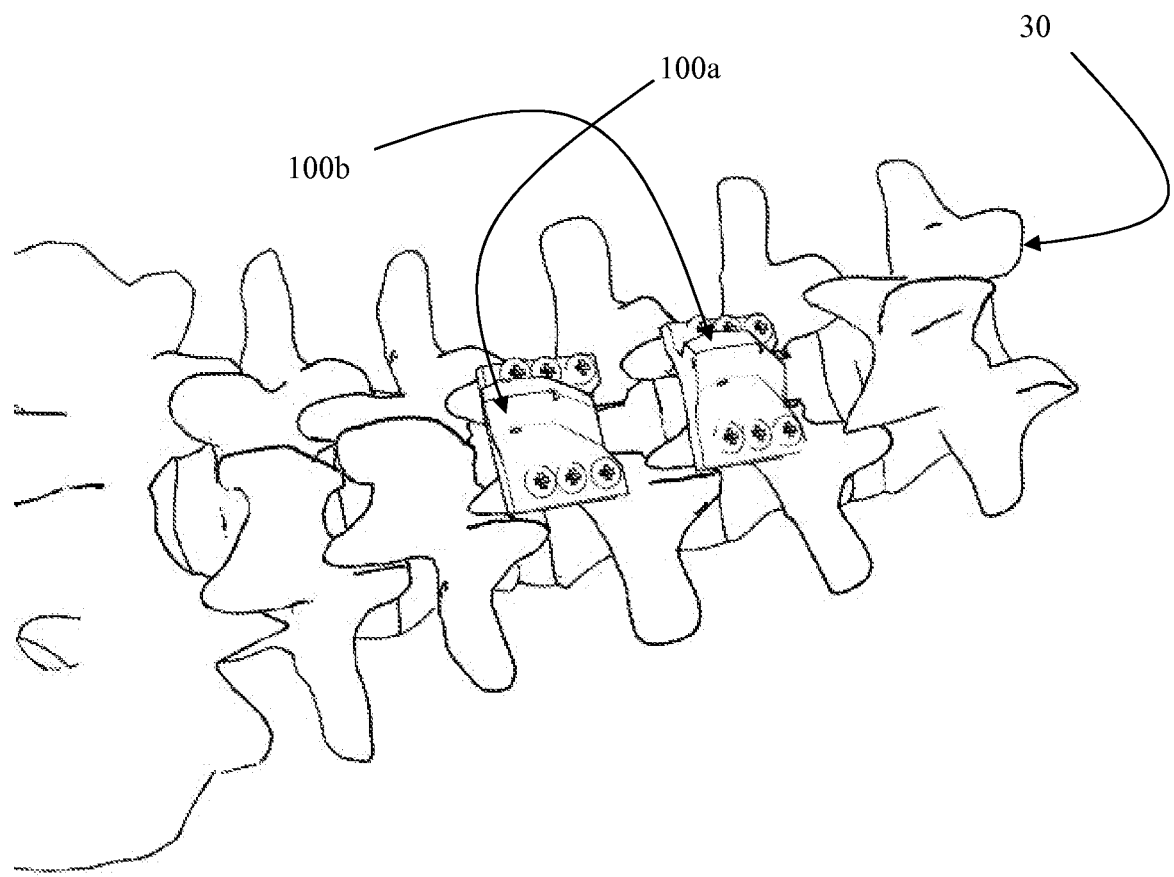
FIG. 5A illustrates an implantation of two Thoracic/Lumbar TASP-LP modules into the Lumbar spine according to an exemplary embodiment (Embodiment IA).
Figure 5B:
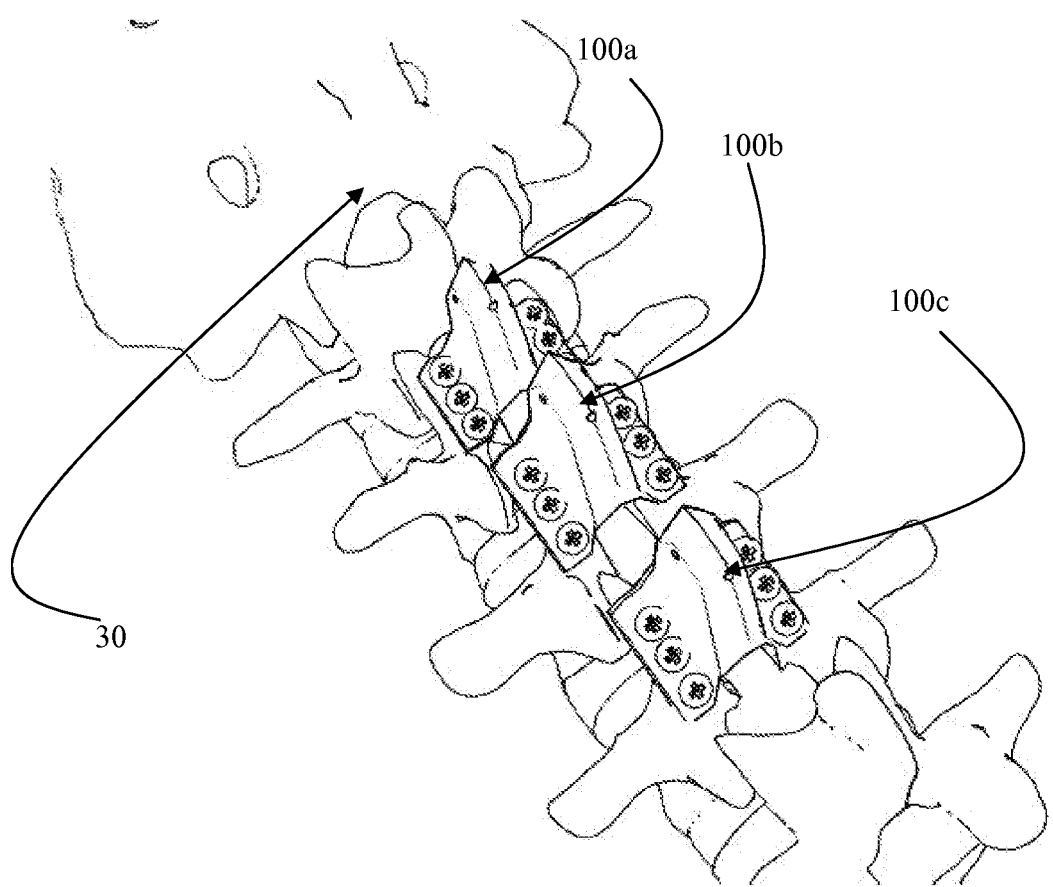
FIG. 5B illustrates an implantation of three Thoracic/Lumbar TASP-LP modules into the Lumbar spine according to an exemplary embodiment (Embodiment IA).

FIGS. 5A and 5B illustrate an exemplary embodiment of a Thoracic/Lumbar TASP-LP 10 (Embodiment IA) that can be modularly applied to two and three level multi-level laminectomies. This embodiment likewise can be applied to four, five, etc. multi-level laminectomies in a modular manner. FIG. 5A illustrates an exemplary embodiment of a Thoracic/Lumbar TASP-LP module 100a, 100b (module #1 and module #2) inserted into a 2 level postlaminectomy natural Lumbar spine 30. FIG. 5B illustrates an exemplary embodiment of TASP-LP modules 100a, 100b, 100c (modules #1, #2, and #3) inserted into the 3-level post-laminectomy natural Lumbar spine 30. In both FIGS. 5A and 5B, the prosthetic modules can reproduce and artificially reconstruct the natural geometry of the spine.

The different modules 100a, 100b, 100c can be manufactured in different heights, lengths, and widths so that the surgeon can select from different sizes to accommodate for differences in patient anatomy.

FIGS. 6A and 6B illustrate other exemplary embodiments of a Thoracic/Lumbar TASP-LP (Embodiments IB and IC, respectively). FIG. 6A illustrates an exemplary embodiment (Embodiment IB) including a double spinous process-laminar prosthetic unit 200a. The prosthetic unit 200a can be, for example, a single piece and can be technically similar to the single module TASP-LP 10 (Embodiment IA) described herein. However, in this embodiment, two modules can be unified into one piece (e.g., integrally formed) with a modular connecting bridge 204 joining the adjacent prosthetic spinous processes 12. Thus, FIG. 6A illustrates the implantation of an exemplary double Thoracic/Lumbar spino-laminar prosthetic module 200a (Embodiment IB) and an exemplary single Thoracic/Lumbar spino-laminar prosthetic module 10 (Embodiment IA) into a 3-level post-laminectomy cervical spine 30. This embodiment can be essentially a hybrid reconstruction. In this manner, the surgeon can choose to replace three natural units with either three (3) single TASP-LP modules (10, 10a, etc.) (Embodiment IA) or with a double TASP-LP module (200, 200a) (Embodiment IB) and a single TASP-LP unit (10, 10a, etc.) (Embodiment IA), or with a single triple TASP-LP module 300 (Embodiment IC) as exemplarily illustrated in FIG. 3B, or with a single triple TASP-LP module 300a as exemplarily illustrated in FIG. 6B. The triple embodiment 300 (FIG. 3B) can include three modules fused, or integrally formed, into one using two modular connecting bridges 302 on the right and left sides of the module 300. The triple embodiment 300a (e.g., as illustrated in FIG. 6A) can include three modules fused into one (e.g., integrally formed), for example, using two modular connecting bridges 304 connecting three modular prosthetic spinous processes 12.

FIGS. 7A-D illustrate an exemplary embodiment of another cervical TASP-LP 400 (Embodiment II). This embodiment differs from Embodiment I in that the prosthesis 400 can include left and right prosthetic laminar hinged extensions 402, 404. These hinged extensions can be attached to the prosthetic lamina 14, 16 with hinge pins 406, 408, for example, as illustrated in FIG. 7D. Thus, the exemplary hinges 406, 408 can be moved up and down like doors allowing individualized accommodating alignment of the TASP-LP 400 with differing natural laminar inclines. FIG. 7A illustrates the laminar hinged extensions 402, 404 in neutral position. FIG. 7B illustrates the laminar hinged extensions 402, 404 in elevated positions. FIG. 7C illustrates the laminar hinged extensions 402, 404 in depressed positions. FIG. 7D illustrates an exploded view of the exemplary embodiment of FIGS. 7A-7C (Embodiment II). The left and right prosthetic laminar hinges 406, 408 can be attached to the hinged TASP-LP prosthesis with pins 410, 412 or other suitable connecting devices. The hinged extensions 402, 404 can rotate about the pin 410, 412 allowing significant up and down movement for allowing placement on varying natural laminar inclines, thereby accounting for patient variability.

FIGS. 8A-D illustrate an exemplary embodiment of a Cervical TASP-LP 500 (Embodiment III). This embodiment differs from the embodiment of FIGS. 7A-7C (e.g., Embodiments I and II), in that the prosthetic spinous process 12 can comprise left and right winged spinous process-laminar hinges 502, 504 which allow elevation or depression of the two hemi-segments of the prosthesis, thus enabling a varying degree of widening of the prosthesis. This embodiment can allow prosthetic accommodation for different laminectomy widths, thereby taking into account differences in inter-patient anatomy, and surgically created laminectomy widths. These two hinged winged hemi-segments 502, 504 can rotate, for example, about a spinous process laminar hinge pin 506, or other suitable part, which provides it with the capacity to accommodate for smaller or larger laminectomy widths. FIGS. 8A, 8B, and 8C illustrate the exemplary embodiment in neutral, elevated and depressed positions, respectively. FIG. 8D illustrates an exploded view of the exemplary embodiment of FIGS. 8A-8C, including the left prosthetic spinous process-laminar hinge 502, the right prosthetic spinous process laminar hinge 504, and the hinge pin 506.

FIGS. 9A and 9B illustrate an exemplary embodiment of a cervical TASP-LP 600 (Embodiment IV). This exemplary embodiment can combine, for example, all the features in Embodiments I, II, and III. For example, the illustrated embodiment includes both left and right prosthetic winged spinous process-laminar hinges 602, 604 which allow movement around a spinous process laminar hinge pin 606, and left and right laminar hinged extensions 608, 610 which allow elevation or depression of these hinges via their rotation around the laminar extension hinge pins 612, 614. Thus, this embodiment can enable accommodation both for differences in varying laminar inclines, by altering the position of its laminar hinge extensions, and for differences in laminectomy widths by widening the device by repositioning the left and right prosthetic spinous-process-laminar hinges 602, 604.

FIGS. 10A-D illustrate an exemplary embodiment of a Thoracic/Lumbar TASP-LP 700 (Embodiment II). This embodiment differs from Embodiment I, in that the embodiment includes left and right prosthetic laminar hinged extensions 702, 704. These hinged extensions 702, 704 can be attached to the prosthetic lamina, for example, with hinge pins 706, 708 as illustrated in FIG. 10D or other suitable devices. Thus, the hinged extensions 702, 704 can be moved up and down like doors allowing individualized alignment of the TASP-LP 700 with the natural incline of different patients' spinal laminar anatomy.

For example, FIG. 10A illustrates the prosthetic laminar hinged extensions 702, 704 in neutral position. FIG. 10B illustrates the prosthetic laminar hinged extensions 702, 704 in elevated positions. FIG. 10C illustrates the prosthetic laminar hinged extensions 702, 704 in depressed position. FIG. 10D illustrates the exploded view of embodiment II. The left and right prosthetic laminar hinged extensions 702, 704 can be attached to the hinged TASP-LP prosthesis, for example, with pins 706, 708 or similar devices. The hinged extensions 702, 704 can rotate about the pin 706, 708 allowing significant up and down movement allowing placement on varying natural inclines accounting for patient anatomical variation.

FIGS. 11A-D illustrate an exemplary embodiment of a Thoracic/Lumbar TASP-LP 800 (Embodiment III). This embodiment differs from Embodiments I and II, in that the prosthetic spinous process 12 can comprise left and right winged prosthetic spinous process-laminar hinges 802, 804 which allow elevation or depression of the two hemi-segments of the prosthesis enabling a varying degree of widening of the prosthesis. This embodiment can allow prosthetic accommodation for different laminectomy widths, thus accounting for differences in inter-patient anatomy, and surgically created laminectomy widths. These exemplary two winged hinged hemi-segments 802, 804 can rotate, for example, about a spinous process laminar hinge pin 806 or other suitable device which provides it with the capacity to accommodate for smaller or larger laminectomy widths. FIGS. 11A, 11B, and 11C illustrate this exemplary embodiment in neutral, elevated and depressed positions, respectively.

FIG. 11D illustrates an exploded view of FIGS. 11A-11C including the left prosthetic winged spinous process-laminar hinge 802, the right winged prosthetic spinous process laminar hinge 804, and the spinous process-laminar hinge pin 806.

FIGS. 12A and 12B illustrate an exemplary embodiment of a Thoracic/Lumbar TASP-LP 900 (Embodiment IV). This embodiment combines all the features in Embodiments I, II, and III and can include, for example, both left and right winged prosthetic spinous process-laminar hinges 902, 904 which allow movement around a spinous process-laminar hinge pin 906 or the like, and left and right laminar hinged extensions 908, 910 which allow elevation or depression of these hinges via their rotation around the laminar extension hinge pins 912, 914. Thus, this embodiment can enable accommodation both for differences in varying laminar inclines, by altering the position of its laminar hinge extensions 908, 910, and for differences in laminectomy widths by widening the device by repositioning the left and right prosthetic winged spinous process-laminar hinges 902, 904.

The exemplary embodiments of a TASP-LP can be made of any bio-compatible material including, for example, polyether ether ketone (PEEK) (e.g., a colourless organic polymer thermoplastic), titanium steel, allograft bone, or other suitable materials, etc.

The exemplary embodiments of a TASP-LP can include pins as well as screws, or other suitable fasteners. The pins can be, for example, flat or round. The pins can include, for example, fish hooks or ridges. The pins can be part of the device or a separate attachment for slots. For example, an apparatus can be used to hold the pin in place while it is being hammered or stapled into the prosthesis.

An exemplary embodiment of the TASP-LP can look like a lamina/spinous process or occupy the space of a lamina/spinous process, or be of any variant shape. The TASP-LP can include, for example, one piece, or two or more pieces assembled together. The pieces can include curves or be straight. The device can have different shapes, such as rectangular, triangular, curved or arch shaped, including for example: triangular arch, round arch, segmental arch, rampant round arch, lancet arc, equilateral pointed arch, shouldered flat arch, cusped arch, horseshoe arch, three centered arch, jack arch, inflexed arch, ogee arch, reverse ogee arch, a parabolic arch, or similar such arcs.

Other exemplary embodiments of the prosthesis can include a joint in the center or the sides for moveability. The exemplary prosthesis can include a ball joint, screw joint, revolute joint, cylindrical joint, gliding joint, mechanical linkage joints, hinges, or any other suitable joint or feature which accomplishes the same function.

Other exemplary embodiments of the prosthesis can comprise bearings, for example, such as a 'bushing' for absorbing shock.

In other exemplary embodiments, the prosthesis can be movable like a clip or hinge. The exemplary prosthesis can be made of flexible material and/or can be spring like.

In another exemplary embodiment, a set or kit of a plurality of prostheses can be provided, each having different standard sizes, such that a surgeon easily can select one or more appropriately sized prostheses. The selected prosthesis each can have the same size or different sizes depending on the dimensions of the natural spinal portions of a given recipient.

The Exemplary Surgical Methods

With reference again to FIGS. 1-12B, exemplary methods including surgical steps for practicing the present invention will now be described.

In an exemplary embodiment, after performing a posterior cervical laminectomy executed by standard surgical technique, the spinous process-bilaminar unit(s) of the cervical post-laminectomy spine can be artificially replaced with a single or multiple cervical TASP-LP modules. Based on a width and length (i.e., number of levels) of the laminectomy, the surgeon selects either a single, multiple, or hybrid number of TASP-LP modules according to one or more of embodiments IA, IB, IC, II, III or IV.

The TASP-LP modules can be secured to the natural lamina on both right and left sides, for example, by screwing in trans-laminar screws through the prosthesis' laminar extension perforations and into the natural remaining lamina. This step can immobilize the construct onto the natural cervical spine. The cervical fascia and muscles then can be reattached to the prosthetic spinous process(es) by passing a suture through the spinous process perforations thereby anatomically reconnecting the muscles to the prosthetic spine thereby mimicking the natural spinal anatomy.

In an exemplary embodiment, after performing a posterior thoracic or lumbar laminectomy executed by standard surgical technique, the spinous process-bilaminar unit(s) of the Thoracic/Lumbar postlaminectomy spine can be artificially replaced with a single or multiple Thoracic/Lumbar TASPLP modules. Based on the width and length (i.e., number of levels) of the laminectomy, the surgeon can select either a single, multiple, or hybrid number of TASP-LP modules according to one or more of embodiments IA, IB, IC, II, III or IV.

The Thoracic/Lumbar TASP-LP modules can be secured to the natural lamina on both right and left sides, for example, by screwing in trans-laminar screws through the prosthesis' laminar extension perforations and into the natural remaining lamina. This can immobilize the construct onto the natural thoracic or lumbar spine. The cervical fascia and muscles can then be reattached to the prosthetic spinous process(es) by passing a suture through the spinous process perforations thereby anatomically reconnecting the muscles to the prosthetic spine thereby mimicking the natural spinal anatomy.

The present invention has been described herein in terms of several preferred embodiments. However, modifications and additions to these embodiments will become apparent to those of ordinary skill in the art upon a reading of the foregoing description.

For example, the exemplary embodiments can include a total artificial spinous process (spino)-laminar prosthesis (TASP-LP) comprising one or more of the features of the cervical and Lumbar embodiments illustrated in embodiments IA, IB, IC, II, III, and IV.

The exemplary embodiments can include a method of replacing the spinous process-bilaminar unit(s) of the cervical postlaminectomy spine with a single or multiple cervical TASP-LP modules according to one or more of embodiments IA, IB, IC, II, III, and IV.

The exemplary embodiments can include a single total artificial spinous process (spino)-laminar prosthesis (TASP-LP) having varying lengths and widths.

The exemplary embodiments can include a plurality of total artificial spinous process (spino)-laminar prosthesis (TASP-LP) having varying lengths and widths.

The exemplary embodiments can include a total artificial spinous process (spino)-laminar prosthesis (TASP-LP) comprising expandable hinged spino-laminar wings to accommodate different laminectomy widths. 6. A total artificial spinous process (spino)-laminar prosthesis (TASP-LP) comprising hinged laminar extensions which can accommodate individualized laminar inclines.

The exemplary embodiments can include a total artificial spinous process (spino)-laminar prosthesis (TASP-LP) comprising both hinged expandable spinous process-laminar wings and hinged laminar extensions.

The exemplary embodiments can include a method of replacing the spinous process-bilaminar unit(s) of the Thoracic/Lumbar post-laminectomy spine with a single or multiple Thoracic/Lumbar TASP-LP modules according to one or more of embodiments IA, IB, IC, II, III, and IV.

The exemplary embodiments can include a total artificial spinous process (spino)-laminar prosthesis (TASP-LP) comprising a biocompatible material.

The exemplary embodiments can include a method of manufacturing tailor made individualized prosthetics using 3-D computerized modeling reconstructions of patients' specific geometric anatomy measured on their CT/Mills.

The exemplary embodiments can include a TASP-LP having two or three screws, as exemplarily illustrated, or with fewer or more screws.

The exemplary embodiments can include a mounting area that can be expanded or have its shape changed to any variety of shapes to cover different areas of the bone for attachment or fixation.

The exemplary embodiments can include a prosthesis having areas for addition or incorporation of bone if a surgeon wishes to include a fusion.

The exemplary embodiments can include screws that are countersunk into the prosthetic surface for fixed locking. Variations of locking mechanisms for fixed or variable angled screws can be applied. Either external or internal locking mechanisms can be employed.

The exemplary embodiments can include a prosthesis that is flexible or expandable in any area.

In other exemplary embodiment, pins and staples can be used instead of screws. Such pin or stapler fixtures can be pounded into the device. Other alternative fixture devices or bonding materials can be used to fixate the prosthesis.

In the exemplary embodiments, the muscle suture attachment can be within the spinous process. This perforation can be a single perforation, or in other embodiments, the prosthesis can include a plurality of perforations, or no perforations. The perforations are not limited to the locations illustrated in the exemplary embodiments and can be located anywhere on the prosthesis.

The exemplary embodiments, the prosthesis can be, for example, manufactured in multiple parts which can come in different sizes accommodating intra-patient and multiple patient anatomical variations, and the prosthesis can be assembled intra-operatively by the surgeon using multiple assembly techniques creating tailor made products individualized for the patient.

In another exemplary embodiment, the method can include selecting one or more appropriately sized prostheses from a set or kit of a plurality of prostheses, wherein the set or kit includes prosthesis having different standard sizes. The selected prosthesis each can have the same size or different sizes depending on the dimensions of the natural spinal portions of a given recipient.

The exemplary embodiments can include a current laminar prosthesis that is arch shaped to mimic the natural spinal, anatomy and to protect the intra-spinal neural elements. However other shapes can also be used which include, but at not limited to, circular, polygonal, pyramidal, flat, cornered, rounded, or any combination, variation, or permutation of the above.

It is intended that all such modifications and additions comprise a part of the present invention to the extent that they fall within the scope of the several claims appended hereto.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper", "lateral", "left", "right" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. The device may be otherwise oriented (rotated 90 degrees or at other orientations) and the descriptors of relative spatial relationships used herein interpreted accordingly.

What is claimed is:

1. A method comprising:
   first, measuring dimensions and geometry of a healthy spine portion of a patient;
   second, generating a 3-dimensional computer rendition of the healthy spine portion of the patient;

third, physically forming a spinal implant for use in implantation into the patient in particular using the 3-dimensional computer rendition of the healthy spine portion of the patient, wherein physically forming the spinal implant comprises physically forming a body, a bifid spinous process having first and second lobes, a first lamina portion, and a second lamina portion to be similar in shape to the healthy spine portion using the 3-dimensional computer rendition of the healthy spine portion; and fourth, coupling the spinal implant to a natural spine of the patient in place of the healthy spine portion of the patient.

2. A method comprising:
first, measuring dimensions and geometry of a healthy spine portion of a patient;
second, generating a 3-dimensional computer rendition of the healthy spine portion of the patient; and
third, physically forming a spinal implant for use in implantation into the patient in particular using the 3-dimensional computer rendition of the healthy spine portion of the patient
fourth, implanting the spinal implant into the patient; and
fifth, attaching the spinal implant to the patient's spine via one or more translaminar or facet screws.

3. The method of claim 1, wherein the healthy spine portion of the patient is a portion of the patient's cervical spine.

4. The method of claim 1, wherein the spinal implant is formed to have the same shape as the healthy spine portion using the 3-dimensional computer rendition of the healthy spine portion.

5. The method of claim 1, wherein the method uses magnetic resonance imaging (MRI) or computerized tomography (CT) imaging techniques to measure dimensions and geometry of the healthy spine portion of the patient.

6. The method of claim 1, wherein the spinal implant comprises a total artificial spinous process (spino)-laminar prosthesis (TASP-LP).

7. The method of claim 1, wherein measuring dimensions and geometry of the healthy spine portion comprises measuring an overall shape, a height, a width, an orientation, and an angulation of the healthy spine portion of the patient.

8. The method of claim 1, wherein the spinal implant has the same slope and angulation of portions of a left side of the patient's Thoracic or Lumbar spine and a right side of the patient's Thoracic or Lumbar spine and the spinal implant is coupled to the natural spine of the patient via screws that are not pedicle screws.

9. The method of claim 1, wherein the method is used in conjunction with performing a laminectomy, and wherein the spinal implant is coupled to the natural spine of the patient after the laminectomy.

10. The method of claim 1, wherein the spinal implant is coupled to the natural spine of the patient via screws that are not pedicle screws.

11. The method of claim 1, wherein the spinal implant is coupled to the natural spine of the patient via one or more translaminar or facet screws.

12. The method of claim 1, wherein the spinal implant has an overall shape, a height, a width, an orientation, and an angulation of the healthy spine portion using the 3-dimensional computer rendition of the healthy spine portion of the patient.

13. The method of claim 2, wherein the method is used in conjunction with performing a laminectomy, and wherein the spinal implant is attached to the patient's spine via one or more translaminar or facet screws after the laminectomy.

14. The method of claim 2, wherein the one or more translaminar or facet screws comprise multiple translaminar screws.

15. The method of claim 2, and further comprising:
performing a laminectomy of the healthy spine portion prior to attaching the spinal implant to the patient's spine via one or more translaminar or facet screws.

16. The method of claim 2, wherein physically forming the spinal implant comprises physically forming a body, a bifid spinous process having first and second lobes, a first lamina portion, and a second lamina portion to be similar in shape to the healthy spine portion using the 3-dimensional computer rendition of the healthy spine portion.

17. A method comprising:
first, measuring dimensions and geometry of a healthy spine portion of a patient;
second, generating a 3-dimensional computer rendition of the healthy spine portion of the patient;
third, physically forming a spinal implant for use in implantation into the patient in particular using the 3-dimensional computer rendition of the healthy spine portion of the patient; and
fourth, coupling the spinal implant to a natural spine of the patient in place of the healthy spine portion of the patient, wherein the spinal implant comprises a first hinged extension that is movable with respect to a portion of the spinal implant and a second hinged extension that is movable with respect to the portion of the spinal implant, wherein the first and second hinged extensions are connected at respective first and second hinges that include respective first and second hinge pins, and wherein the first and second hinge pins are aligned substantially in a rostral-to-caudal direction when the spinal implant is coupled to the natural spine.

18. A method comprising:
first, measuring dimensions and geometry of a healthy spine portion of a patient;
second, generating a 3-dimensional computer rendition of the healthy spine portion of the patient;
third, physically forming a spinal implant for use in implantation into the patient in particular using the 3-dimensional computer rendition of the healthy spine portion of the patient, wherein the spinal implant formed using the 3-dimensional computer rendition comprises first, second, and third portions that are interconnected and movable with respect to one another; and
fourth, coupling the spinal implant to a natural spine of the patient in place of the healthy spine portion of the patient.

19. The method of claim 18, and further comprising:
moving the first and third portions with respect to the second portion.

20. A method comprising:
first, measuring dimensions and geometry of a healthy spine portion of a patient;
second, generating a 3-dimensional computer rendition of the healthy spine portion of the patient;
third, physically forming a spinal implant for use in implantation into the patient in particular using the 3-dimensional computer rendition of the healthy spine portion of the patient, wherein the spinal implant comprises at least three modules with at least two of the modules formed to have the same shape as the healthy spine portion of the patient, wherein the at least three modules each includes an artificial spinous process and wherein the artificial spinous processes are interconnected left and right modular connecting bridges; and
fourth, coupling the spinal implant to a natural spine of the patient in place of the healthy spine portion of the patient.

* * * * *